United States Patent
Saint-Pierre et al.

(10) Patent No.: US 10,130,735 B2
(45) Date of Patent: Nov. 20, 2018

(54) SCAFFOLD FOR CARDIAC PATCH

(71) Applicants: Tecnologías Avanzadas Inspiralia, S.L., Madrid (ES); The University of Manchester, Manchester, Lancashire (GB); Institutul de Chimie Macromoleculara Petru Poni, Iasi (RO); Ustav Experimentalni Mediciny Akademie Ved Ceske Republiky Verejna Vyzkumna Instituce, Prague (CZ)

(72) Inventors: Guillaume Saint-Pierre, Madrid (ES); Miguel Herrero Gomez, Madrid (ES); Sandra Martinez Crespiera, Madrid (ES); Alberto Saiani, Manchester (GB); Catherine Merry, Manchester (GB); Kate Meade, Manchester (GB); Jean-Baptiste Guilbaud, Manchester (GB); Aline Fiona Miller, Manchester (GB); Constentin Ciobanu, Iasi (RO); Evzen Amler, Prague (CZ)

(73) Assignees: Technologias Avanzadas Inspiralia S.L., Madrid (ES); The University of Manchester, Manchester (GB); Institutut de Chimie Macromoleculara Petru Poni, Iasi (RO); Ustav Experimentatni Mediciny Akademie Ved Ceske Republiky Verejna Vyzkumna Instituce, Prague (CZ)

( * ) Notice: Subject to any disclaimer, the term of this patent is extended or adjusted under 35 U.S.C. 154(b) by 698 days.

(21) Appl. No.: 14/429,683

(22) PCT Filed: Sep. 21, 2012

(86) PCT No.: PCT/EP2012/068648
§ 371 (c)(1),
(2) Date: Mar. 19, 2015

(87) PCT Pub. No.: WO2014/044321
PCT Pub. Date: Mar. 27, 2014

(65) Prior Publication Data
US 2015/0246157 A1    Sep. 3, 2015

(51) Int. Cl.
| | |
|---|---|
| *A01N 61/00* | (2006.01) |
| *A61K 31/00* | (2006.01) |
| *A61L 27/18* | (2006.01) |
| *A61L 27/34* | (2006.01) |
| *A61L 27/38* | (2006.01) |
| *A61L 27/50* | (2006.01) |
| *A61L 27/52* | (2006.01) |
| *A61L 27/54* | (2006.01) |
| *A61L 27/58* | (2006.01) |
| *A61L 27/22* | (2006.01) |
| *A61L 27/36* | (2006.01) |

(52) U.S. Cl.
CPC ............. *A61L 27/18* (2013.01); *A61L 27/227* (2013.01); *A61L 27/34* (2013.01); *A61L 27/3604* (2013.01); *A61L 27/38* (2013.01); *A61L 27/502* (2013.01); *A61L 27/52* (2013.01); *A61L 27/54* (2013.01); *A61L 27/58* (2013.01); *A61L 2300/414* (2013.01); *A61L 2300/43* (2013.01); *A61L 2300/626* (2013.01); *A61L 2430/20* (2013.01)

(58) Field of Classification Search
CPC ........ C08L 2666/26; C08L 5/00; C08L 75/04; A61K 2300/00
See application file for complete search history.

(56) References Cited

FOREIGN PATENT DOCUMENTS

| WO | WO-2006036826 | 4/2006 | |
|---|---|---|---|
| WO | WO-2011134957 | 11/2011 | |
| WO | WO-2012045822 A1 * | 4/2012 | ....... A61K 47/48176 |

OTHER PUBLICATIONS

PCT International Preliminary Report on Patentability dated Mar. 24, 2015, PCT Appln. No. PCT/EP2012/068648, 6 pages.
Batista, Randas J., et al., "Partial Left Ventriculectomy to Treat End-Stage Heart Disease", *Ann Thorac Surg*, vol. 64, (1997), 634-8.
Bolognese, Leonardo, et al., "Left Ventricular Remodeling After Primary Coronary Angioplasty: Patterns of Left Ventricular Dilation and Long-Term Prognostic Implications", *Circulation*, vol. 106, (2002), 2351-2357.
Callegari, Andrea, et al., "Neovascularization induced by porous collagen scaffold implanted on intact and cryoinjured rat hearts", *Biomaterials*, vol. 28, (2007), 5449-5461.
Davis, Michael E., et al., "Custom Design of the Cardiac Microenvironment With Biomaterials", *Circulation Research*, vol. 97, (2005), 8-15.

(Continued)

Primary Examiner — Rachael E Bredefeld
Assistant Examiner — Kaipeen E Yang
(74) Attorney, Agent, or Firm — Womble Bond Dickinson (US) LLP

(57) ABSTRACT

A biocompatible and biodegradable medical device patch actuating primarily as soft tissue structural reinforcement. The device has a layered architecture, where the primary serves as suturing layer and mechanical support to a thick porous scaffold which can be coated with a mimic-like extra cellular matrix (ECM). The device can be provided to the end user under the format of independent layers that can be cut and assembled to the specific need to the end user and patient. The layers are assembled without the need of any adhesive. Totally haemocompatible and of behavior superior to polytetrafluoroethylene used for any soft tissue repaired, the field of this invention is demonstrated for cardiovascular therapy but should not be limited to it. It is of practical relevance of vein, tendon and hernias and dermal treatments.

20 Claims, 33 Drawing Sheets
Specification includes a Sequence Listing.

(56) References Cited

OTHER PUBLICATIONS

Dor, V., et al., "Efficacy of Endoventricular Patch Plasty in Large Postinfarction Akinetic Scar and Severe Left Ventricular Dysfunction: Comparison With a Series of Large Dyskinetic Scars", *The Journal of Thoracic and Cardiovascular Surgery*, vol. 116, No. 1, (Jul. 1998), 50-59.

El Fray, Miroslawa, et al., "Novel hybrid PET/DFA—TiO2 nanocomposites by in situ polycondensation", *Materials Letters*, vol. 59, (2005), 2300-2304.

Freed, Lisa E., et al., "Advanced Material Strategies for Tissue Engineering Scaffolds", *Advanced Materials*, vol. 21, (2009), 3410-3418.

Fujimoto, Kazuro L., et al., "An Elastic, Biodegradable Cardiac Patch Induces Contractile Smooth Muscle and Improves Cardiac Remodeling and Function in Subacute Myocardial Infarction", *Journal of the American College of Cardiology*, vol. 49, No. 23, (Jun. 12, 2017), 2292-2300.

Godier-Furnémont, Amandine F., et al., "Composite scaffold provides a cell delivery platform for cardiovascular repair", *PNAS*, vol. 108, No. 19, (May 10, 2011), 7974-7979.

Grossman, P. M., et al., "Incomplete Retention After Direct Myocardial Injection", *Catheterization and Cardiovascular Interventions*, vol. 55, (2002), 392-397.

Hai, S., et al., "Relationship Between Changes in Heart Rate Recovery After Cardiac Rehabilitation on Cardiovascular Mortality in Patients with Myocardial Infarction", *JACC*, vol. 55, No. 10A, (Mar. 9, 2010), A59.E568.

Hoffman, Allan S., "Hydrogels for biomedical applications", *Advanced Drug Delivery Reviews*, vol. 43, (2002), 3-12.

Hofmann, Michael, et al., "Monitoring of Bone Marrow Cell Homing Into the Infarcted Human Myocardium", *Circulation*, vol. 111, (2005), 2198-2202.

Jawad, Hedeer, et al., "Myocardial tissue engineering", *British Medical Bulletin*, vol. 87, (2008), 31-47.

Jawad, H., "Myocardial tissue engineering: a review", *J Tissue Eng Regen Med*, vol. 1, (2007), 327-342.

Laflamme, Michael A., et al., "Regenerating the heart", *Nature Biotechnology*, vol. 23, No. 7, (Jul. 2005), 845-856.

Ott, Harald C., et al., "Perfusion-decellularized matrix: using nature's platform to engineer a bioartificial heart", *Nature Medicine*, vol. 14, No. 2, (Feb. 2008), 213-221.

Pfeffer, Marc A., et al., "Ventricular Remodeling After Myocardial Infarction: Experimental Observations and Clinical Implications", *Circulation*, vol. 81, No. 4, (1990), 1161-1172.

Piao, Hainan, et al., "Effects of cardiac patches engineered with bone marrow-derived mononuclear cells and PGCL scaffolds in a rat myocardial infarction model", *Biomaterials*, vol. 28, (2007), 641-649.

Pozzobon, M., et al., "Human Bone Marrow-Derived CD133+ Cells Delivered to a Collagen Patch on Cryoinjured Rat Heart Promote Angiogenesis and Arteriogenesis", *Cell Transplantation*, vol. 19, 2010, 1247-1260.

Sarig, Udi, et al., "Engineering cell platforms for myocardial regeneration", *Expert Opinion on Biological Therapy*, vol. 11, No. 8, (2011), 1055-1077.

Savoye, Christine, et al., "Left Ventricular Remodeling After Anterior Wall Acute Myocardial Infarction in Modern Clinical Practice (from the REmodelage VEntriculaire [REVE] Study Group)", *The American Journal of Cardiology*, vol. 98, (2006), 1144-1149.

Sutton, Martin S., et al., "Quantitative Two-dimensional Echocardiographic Measurements Are Major Predictors of Adverse Cardiovascular Events After Acute Myocardial Infarction: The Protective Effects of Captopril", *Circulation*, vol. 89, No. 1, (Jan. 1994), 68-75.

Ye, Zhaoyang, et al., "Myocardial regeneration: Roles of stem cells and hydrogels", *Advanced Drug Delivery Reviews*, vol. 63, (2011), 688-697.

\* cited by examiner

*Melt processing and further HF treatment*

*Freeze/Phase Inversion*

Stress-Strain curve of the PCL-3 scaffolds.
Elongation at break 191 %; Tensile strength 1.061MPa;
Hardness 1.5665.705MPa Stress-Strain curve of the Copolymer 2. Elongation at break 257 %; Tensile strength 1.3674 MPa; Hardness 3.1229MPa

Stress vs. strain curve of the PCL 3 scaffold up to the elastic limit. Ei=6.005MPa; Ue = 0.0048 MPa

Stress vs. strain curve of the Copolymer 3 up to the elastic limit. Ei = 5.2164 MPa; Ue = 0.0053MPa

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Self assembling peptide

<400> SEQUENCE: 1

Phe Glu Phe Glu Phe Lys Phe Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Self assembling peptide

<400> SEQUENCE: 2

Val Glu Val Glu Val Lys Val Lys
1               5

<210> SEQ ID NO 3
<211> LENGTH: 12
<212> TYPE: PRT
<213> ORGANISM: Artificial Sequence
<220> FEATURE:
<223> OTHER INFORMATION: Self assembling peptide

<400> SEQUENCE: 3

Pro Gly Ser Pro Phe Glu Phe Glu Phe Lys Phe Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Self assembling peptide

<400> SEQUENCE: 4

Ile Gly Phe Phe Glu Phe Glu Phe Lys Phe Lys
1               5                   10
```

SCAFFOLD FOR CARDIAC PATCH

CROSS-REFERENCE TO RELATED APPLICATIONS

The present patent application is a national phase application of International Application No. PCT/ES2012/068648, filed Sep. 21, 2012, the disclosure of which is incorporated herein by reference.

SEQUENCE LISTING

An electronic copy of the Sequence Listing entitled "PCT26091_ST25.txt" is incorporated herein by reference. This Sequence Listing consists of [SEQ ID NOs: 1-4].

BACKGROUND OF THE INVENTION

Cardiovascular disease (CVD) is a major health problem and the leading cause of death in the western world. In the United Kingdom, for example, CVD accounts for 238,000 deaths, comprising 39% of all deaths per annum (Jawad et al. J Tissue Eng. Regen. Med. 2007, 1, 327). Heart attacks are the main cause of death in patients with CVD. Approximately 30% of the 270,000 patients suffering from heart attacks each year die suddenly before reaching the hospital. The adult heart cannot repair the damaged tissue, as the mature contracting cardiomyocytes are unable to divide. The result of the myocardial infarction is the formation of scar tissue with different contractile, mechanical and electrical properties to that of normal myocardium, which is unable to deliver sufficient blood to meet the body's metabolic requirements.

There is a great deal of interest in developing new methods to repair and regenerate the infarcted area of the myocardium. Replacement of scarred tissue with skeletal muscle cells, cells derived from bone marrow (mesenchymal and hematopoietic) or embryonic stem cells (ESCs) have been proposed (Laflamme, M. A. and Murry, C. E. Nature Biotechnology 2005 23, 845). Currently the preferred method of introducing these cells into the dead myocardium is injection of cells in suspension into either the circulating blood or directly into the myocardium. The cell delivery route is in principle inefficient with substantial cell loss (Hofmann M.; et al Circulation 2005, 111, 2198; Grossman P. M.; et al Catheterization and cardiovascular interventions 2002, 55, 392). This has prompted search for alternative delivery techniques for the cells, such as tissue engineering (TE).

Myocardial tissue engineering (MTE), a concept that intends to prolong patients' lives after myocardial infarction by restoring myocardial function, is continuously improving.

Many different cell types have been suggested for cell therapy and myocardial tissue engineering. These include both autologous and embryonic stem cells. Biomaterials suggested for this specific tissue engineering application need to be biocompatible with the cardiac cells and have particular mechanical properties matching those of native myocardium so that the delivered donor cells integrate and remain intact in vivo.

The aim of cardiac tissue engineering (CTE) is to repair or regenerate a damaged section of the heart. CTE involves the synthesis of a scaffold or patch made from a biomaterial combined with cells.

In a cell therapy perspective, the main function of the biomaterial is to act as a vehicle for the delivery of cells to the damaged area, i.e. scarred tissue. Once cells are delivered to the desired region, the cells should integrate with the host tissue forming new myocardium.

Biomaterials research is a broad subject and candidate biomaterials suitable for CTE patches are being continuously sought. A great variety of synthetic and natural polymers, as well as composite materials, have been proposed for CTE.

To focus on the cardiac patch approach, a significant proportion of patient population develop left ventricular (LV) enlargement despite recent progresses in coronary perfusion and drug based medical therapies. This situation is provoked by the remodeling process following myocardial infarction (MI) (Bolognese, L.; Neskovic, A. N.; Parodi, G.; Cerisano, G.; Buonamici, P.; Santoro, G. M. Circulation 2002; 106:2351-7, Savoye, C.; Equine, O.; Tricot, O.; Nugue, O.; Segrestin, B.; Sautiere K. Am J Cardiol 2006; 98, 1144-9., and Pfeffer, M. A.; Braunwald, E. Circulation, 1990; 81; 1161-72). Post-MI LV remodeling is associated with maladaptive myocardial changes in both infarcted and non infarcted areas (Pfeffer, M. A.; Braunwald, E. Circulation 1990; 81, 1161-72), resulting in LV enlargement and systolic function impairment, which in turns increase the risk of heart failure followed by death (Pfeffer, M. A.; et al. Circulation 1994; 89; 6875 and Pfeffer, M. A., et al. Circulation 1994, 89, 6875).

Different surgical approaches have been proposed to reduce the LV cavity volume (Dor, V.; et al. J. Thorac. Cardiovasc. Surg 1998; 116, 50-9) or restricting its further enlargement (Batista, R. J.; et al Ann Thorac Surg 1997, 64, 634e8.) to patients suffering refractory heart failure (HF) from severe LV dilation and dysfunction. In a general manner, these methods are based on major reconstructive surgery or involve extension encapsulation (contention) of the epicardium.

It has been demonstrated a cardiac patch implanted after MI can present LV remolding and definitively improves cardiac performance.

Using a two layers, biocompatible poly(propylene)/expanded polytetrafluoroethylene (PP/PTFE), Hung Fat Tse et al (J Am College Cardio, 2010, 58, 590-598) validated the need for a cardiac patch concept, whereby a simple, passive synthetic epicardial patch is employed to increase LV wall thickness at the infarct region, attenuate LV dilation and improve of left ventricular ejection fraction (LVEF) in a large animal model of chronic MI.

Initially reported as vector for cellular therapy, the utilization of cardiac patch as a biomaterial has moved towards accelular therapy whereby the device is foreseen as a medical device providing a medical support as principal mode of action, where the microenvironment and architecture offer additional advantages such as cellular differentiation, organization and prevention of anoikis (Sarig, U., Machluf, M. Expert Opin Biol Ther 2011, 11, 1055-77). However today's main limitation remain cross and trans scaffold diffusion controlled nutrient transport.

Among the different materials proposed for the fabrication of such device, collagen has been extensively used as reported in subsection polymers in CTE. Such protein scaffold is compatible is angiogenesis process (Callegari, A.; et al. Biomaterials 2007, 28, 5449-61.) and cellular therapy (Pozzobon, M., et al. Cell transplantation 2010, 19, 1247-6).

Decellularized organs (Ott, H. C., et al. Nat Med 2008, 14, 213-21 and Godier-Furnémont, A. F., et al. Proc Natl Acad Sci USA 2011; 108, 7974-9.) have also been proposed for the creation of cardiac patches. Despite the limited number of studies using an organ-derived scaffold in the heart, to date, example of using decellularised bovin aortic valve in heart valve replacement therapy suggest a rapid expansion of decellularized scaffolds in tissue engineering.

Apart from biologically derived materials, a number of synthetic materials have been explored, such as biodegradable polyester urethane (Fujimoto, K. L., et al., J Am Coll Cardiol, 2007, 49, 2292-300) or poly(glycolide-co-caprolactone) (Piao, H.; et al. Biomaterials 2007, 28, 641-9) for cellular and acellular therapy.

Despite thought to be resilient with functional environment in which they are foreseen to operate, scaffold functionalization to provide biological cues is still a center of debate as one should take into consideration the bio-availability of the immobilized agent and its concentration profile over the supramolecular architecture.

Softer scaffolds such as hydrogels have also been proposed for acellular therapies, drug delivery system and support vector for cell delivery and in-vitro cardiac tissue engineering (Ye, Z.; et al. Advanced Drug Delivery Reviews, 2011, 63, 688-697). Such types of biomaterials are considered to provide extra cellular matrix (ECM)-like chemical and biophysical environment thus, thereby offering a proper resort for improving the retention, survival, and function of transplanted and recruited cardiogenic cells (Davis, M. E.; et al. Circ. Res. 2005, 97, 8-15 and Jawad, H.; et al. Br. Med. Bull. 2008, 87, 31-47)

Indeed, a 3D gel may represent an advanced culture system for in vitro cell expansion and the induction of cardiogenic differentiation, wherein cardiogenic differentiation of stem cells can occur through the occurrence of biochemical, topographic and physical cues. While poly(N-isopropylacrylamide)(PNiPAmm) has been proposed for in-vitro cell sheet engineering (Jawad, H., et al. Br. Med. Bull. 2008, 87, 31-47), other polymers such as collagen, fibrin, alginate and PEG and peptides have been evaluated for their ability to form hydrogels in cardiac cell therapy/tissue engineering.

While hydrogels provide new possibilities for addressing certain issues, such as controlling stem cell differentiation in vitro and in vivo experiments through simple scaffold fictionalization procedure such as entrapment and creation of cell signaling agent concentration gradient and cell delivery, their success in cardiac tissue engineering, as so far, has been limited due to associated weak mechanical properties to allow such architecture to wisthand beating environment in vivo and possible complete wash due to exposure to body fluids (Freed, L. E.; et al. Adv. Mater. 2009, 21, 3410-3418).

Therefore, it would be desirable to develop a biomaterial based 'vehicle', based on a porous scaffold or dense patch, made of either natural or synthetic polymeric materials to aid transportation of cells into the diseased region in the heart.

SUMMARY OF THE INVENTION

The present invention relates to a multilayered architecture primarily oriented as a medical device developed for the structural reinforcement of a damaged soft tissue. It comprises a porous polyurethane base and a thick porous scaffold based on poly(ε-caprolactone)/natural polymers composites. Optionally, it can be combined with self assembled gels composed of, but not limited to, peptides and polyurethanes. The device application is useful in cellular therapy.

DESCRIPTION OF THE INVENTION

One aspect of the present invention relates to a composition comprising:

a)—a biocompatible and biodegradable scaffold comprising synthetic and natural polymers, wherein the synthetic polymer is selected from polylactic acid, glycolic acid, lactone, polyglicerol sebacate, copolymer of synthetic polymers and combinations thereof, and wherein the natural polymer is selected from chitosan, sodium alginate and cellulose;
b)—a hydrogel comprising self assembling peptides, wherein the self assembling peptides are selected from FEFEFKFK (SEQ ID NO: 1), VEVEVKVK (SEQ ID NO: 2), PGSPFEFEFKFK (SEQ ID NO: 3), IGF-FEFEFKFK (SEQ ID NO: 4) and combinations thereof; and
c)—a support comprising polyurethane.

Another aspect of the present invention relates to the composition as defined above for use in therapy.

Another aspect of the present invention relates to the composition as defined above for use in the treatment of a patient with curretage or transmural infarct treatment, preferably in the treatment of myocardial infraction, and more preferably wherein the treatment comprises cardiac tissue regeneration.

Another aspect of the present invention relates to the use of the composition as defined above for in vitro methods.

Another aspect of the present invention relates to a cardiac patch comprising the composition as defined above.

Another aspect of the present invention relates to a cardiac patch comprising the composition as defined above for use in the treatment of myocardial infraction.

Another aspect of the present invention relates to a process to obtain the composition as defined above which could either comprise:
i.—melting blending wherein all organic and inorganic components are mixed together in an Haake;
ii.—treatment with hydrofluoric acid; mediated dissolution of glass porogen followed by thorough wash for scaffold pH neutralisation
iii Removal of Acid
iii.—introducing the self-assembling peptide into the polymers by centrifugation gravity or simple impregnation;
iv.—drying; and
v.—sterilization.

Another aspect of the present invention relates to a process to obtain the composition as defined above which could either comprise:
i. material dissolution
ii solvent casting and cold precipitation
iii solvent extraction
iv introducing the self-assembling peptide into the polymers by centrifugation or gravity
iv.—drying; and
v.—sterilization.

In a preferred embodiment, the process as described above, further comprises—production of fibers by electrospinning; and deposition of the electrospun fibers onto the polymers by coaxial electrospining, wherein these steps are performed between steps (i) and (ii)

Another aspect of the present invention relates to a process to obtain the composition as defined above which comprises a freeze/phase inversion. In a preferred embodiment, the process as described above, further comprises—production of fibers by electrospinning; and deposition of the electrospun fibers onto the polymers by coaxial electrospining, wherein these steps are performed between steps (i) and (ii)

Another aspect of the present invention relates to a method for treating a patient with myocardial infraction which consists in the implantation of the cardiac patch, as defined above, in the heart pericardium, preferably in the surface of the heart pericardium by suture of the support or through the heart pericardium and myocardium by suture of the support.

A long the description of the present invention, the term "scaffold" refers to a engineered material platform that can be formed in the shape of tissue that needs to be replaced (as an example a rotator cuff). The scaffold can be biologically derived or a synthesized material. The scaffold material must be biologically compatible for human implantation. The scaffold is typically impregnated (seeded) with a patient's cells before implantation. The scaffold must be designed to "degrade" as the cells grow on the scaffold. Typically, in several months, the scaffold has disappeared and has been replaced by new tissue.

A scaffold is therefore a 3D construct that serves as temporary support for isolated cells to grow into new tissue either in vitro, i.e. before transplantation back to the host or in vivo, i.e. once implanted.

The design of the scaffold determines the functionality of the construct to a high extent. Although the final requirements depend on the specific purpose of the scaffold, several general characteristics and requirements need to be considered for all designs.

The scaffold should be:
biocompatible; the scaffold should provoke an appropriate biological response in a specific application and prevent any adverse response of the surrounding tissue.
biodegradable; the scaffold materials should degrade in tandem with tissue regeneration and remodeling of the extracellular matrix (ECM) into smaller non toxic substances without interfering with the function of the surrounding tissue.
promote cell attachment, spreading and proliferation; vital for the regulation of cell growth and differentiation.
suitable mechanical strength; its strength should be comparable to in vivo tissue at the site of implantation as evidently, a scaffold requires more flexibility or rigidity depending on the application in e.g. cardiovascular versus bone prostheses.
good transport properties; to ensure sufficient nutrient transport towards the cells and removal of waste products the scaffold should be highly porous with good pore connectivity, however, it should maintain sufficient mechanical strength implying optimization of porosity.
easy to connect to the vascularization system of the host; to ensure good nutrient supply throughout the scaffold post-implantation, the scaffold should be connected to the natural nutrient supplying system
suitable surface characteristics; apart from optimal physiochemical properties, research suggests that the introduction of e.g. surface topography into the scaffold improves tissue organization leading to increased tissue function The term "hydrogel" can be defined as a crosslinked polymeric network which has the capacity to hold water within its porous structure. The water holding capacity of the hydrogels arise mainly due to the presence of hydrophilic groups, viz. amino, carboxyl and hydroxyl groups, in the polymer chains. According to Hoffmann (2002) (Hoffman A S. Hydrogels for biomedical applications, Advanced Drug Delivery Reviews 2002; 54: 3-12), the amount of water present in a hydrogel may vary from 10% to thousands of times of the weight of the xerogel, where the xerogel is defined as a polymeric network devoid of water. The water holding capacity of a xerogel is dependent on the number of the hydrophilic groups and crosslinking density. Higher the number of the hydrophilic groups, higher is the water holding capacity while with an increase in the crosslinking density there is a decrease in the equilibrium swelling due to the decrease in the hydrophilic groups. As the crosslinking density increases, there is a subsequent increase in the hydrophobicity and a corresponding decrease in the stretchability of the polymer network.

Hydrogels are crosslinked polymeric networks and hence provide the hydrogel with a 3-dimensional polymeric network structure.

Hydrogels can be sub-categorized into 2 groups accordingly to the nature of their crosslinking. As such, some might be considered as permanent hydrogels where crosslinking involves the formation of covalent bonds. Physical hydrogels as those derived from self assembled peptides or natural are formed due to the physical interactions, viz. molecular entanglement, ionic interaction and hydrogen bonding, among the polymeric chains.

A "patch" refers to one form of transdermal formulation whose application is for systemic therapy.

"CTE" refers to a materials-based approach; and involves pre-formed 3-dimensional scaffolds, in the form of mesh, patch or foam, being cultured with cells (either cardiac or non-cardiac).

"Plasticizers" are small low molecular weight compounds added to polymers to reduce brittleness and glass transition temperature, impart flexibility, and enhance toughness for films "Polymers in MTE" refer to polymers, both natural and synthetic, are the largest class of engineered biomaterials used today for myocardial tissue reconstruction; they are available in a wide variety of compositions and properties.

The development of synthetic polymers has led to an astonishing success rate for soft tissue implants, due to the fact that polymers can be tailor-made to match the properties of soft tissues.

Thermoplastic elastomers, specifically, nanostructured multiblock (segmented) copolymers, multiblock polyurethanes for example are recognized as key polymers in the medical field being among the most bio—and blood-compatible known today (El-Fray M., et al. Materials Letters 2005, 59, 2300). Some of the first polymeric materials used for heart tissue engineering (patches) were based on hydrolytically degradable biocompatible polymers composed of polylactic acid (PLA), polyglycolic adic (PGA) and their copolymer polylactic-co-glycolic acid (PLGA). With increasing research and experimental trials, it has been established that elastic properties of the biomaterial must match the elastic properties of the native heart as closely as possible to prevent the cells detaching from the bioengineered construct, thus alternative polymers are continuously being developed.

TABLE 1

Example of selected polymers reported for cardiac patch application

| Polymer type | Comments | Application |
| --- | --- | --- |
| Synthetic polymers | | |
| Polyurethane | Support for Cell sheet culture Biodegradable elastomer | Lamini functionalised contension |
| 1,3-trimethylene carbonate copolymers | Able to sustain cyclic loads of heart muscle | contension |

TABLE 1-continued

Example of selected polymers reported for cardiac patch application

| Polymer type | Comments | Application |
|---|---|---|
| Poly(ε-caprolactone) | Cell seeding | Support differentiated beating cardiomyocites |
| poly(n-isoprolyacrylamide) (PiPAAm) | Non implantable polymer | Cell sheet engineering |
| *Natural polymers* | | |
| Polygycolic acid | Commercially available | Seeded with extracellular matrix (ECM), support ventricular function |
| Collagen | Exogenous material No improvement of ventricular function and immunogenicity issues when implanted in vivo | In vitro electrosimulation Cell sheet engineering |
| | Mixed with Matrigel or glycosaminoglycan | Cell sheet engineering |
| Gelatin (Gelafoam) | Does not provide lead to any functional improvement of ventricular function | Support seeded beating cardyomyocite |
| Alginate Chitosan | Risk of necrosis and calcification | In-vitro cell culture and seeded cardiac patch |
| *Natural-synthetic composites* | | |
| Poly(ester-urethane)-Collagen | Use of the mechanical properties of the synthetic components and cellular adhesion properties of the collagen | In vitro cell culture |
| Poly(ε-caprolactone)-Collagen | Use of the mechanical properties of the synthetic components and cellular adhesion properties of the collagen | In vitro cell culture |
| Poly(D,L-lactide-co-caprolactone)-Collagen | Use of the mechanical properties of the synthetic components and cellular adhesion properties of the collagen | In vitro cell culture |
| Poly(glycerol-sebaccate)-Gelatin | No results regarding contractility or in vivo assays | Cell differentiation |

As in general TE approaches, the selection of biocompatible and biodegradable biomaterials and the design of patches for heart muscle engineering could be guided by the following criteria: (i) ability to deliver and foster cells, (ii) biodegradability, (iii) biocompatibility, and (iv) appropriate mechanical properties. Porosity is another important factor to be considered, in particular, for 3D tissue engineering constructs.

As in general TE approaches, the selection of biomaterials and the design of patches for heart muscle engineering could be guided by the following criteria:
(i) ability to deliver and foster cells,
(ii) biodegradability,
(iii) biocompatibility
(iv) appropriate mechanical properties.
(v) Porosity is another important factor to be considered, in particular, for 3D tissue engineering constructs.

Biodegradability is not always essential, depending on the applied approaches for cardiac tissue engineering. Degradable polymers, including natural and synthetic, are applied in the heart patch approach and, in particular, in 3D tissue engineering construction.

In relation to mechanical properties, there are no strict requirements on the mechanical properties of the biomaterials used for patch, as long as it provides a mechanical support at the end of diastole.

Practically, however, a patch should have optimal compliance so as to smoothly fit on the surface of the heart. Moreover, it would be ideal that the supporting device exhibits a nonlinear elasticity of heart muscle such that it could reshape with the heart and thus provide mechanical support to the heart throughout the beating processes, rather than only at the end of diastole. One specific benefit of the heart patch approach could be simple changes in ventricular geometry and mechanics leading to a reduction of elevated local wall stresses.

Issues other than biocompatibility, biodegradability and mechanical properties such as cues (physical, chemical and biological) must be provided to promote cellular adhesion, expansion and differentiation.

For the cells to survive and carry out their full potential functions they must be embedded in a 3D scaffold containing pores. In this scenario, it should be considered the required functions of the engineered construct. If the patch is to act solely as a "vehicle" to transport the cells into the patient, and then degrade in a short period (e.g. within 3 months), a dense patch would be suitable. Alternatively, if the construct is to support the damaged area for a sustained period, then it is vital that it provides a porous structure, amongst many other factors, to ensure cell survival for the time they are in contact with the scaffold.

Further The polymeric support not only serve at easing surgical procedure for device immobilization, in this sense a sewable support: but also positively contribute to the mechanical properties of the overall device.

Summarizing, the principal aspects of the final devices are as follows:

Porosity: two pore sizes should be distributed into the scaffold matrix. Pores of at least 100 μm are necessary to fit cell sizes, but also intrastructural pores of 10 μm are necessary for cell rooting Patch thickness: the patch should be at least 500 μm thick Mechanical properties: The patch stiffness should be similar or even higher than that of the human myocardium. As reference, the mechanical properties of the human myocardium are described as follow:
Young's modulus: 0.2-0.5 MPa
Tensile strength: 3-15 kPa Biodegradation: Degradation should be completed in 6 months, either of the mass level or of the mechanical properties. The option will also be considered of a very slowly degradable material, that would provide mechanical support to the ventricular wall for longer periods.

Vascularization: The neo-vascularization is a fundamental requirement of the engineered cardiac tissue. The aim is to have 2400-3300 capillaries/mm2, ~20 μm intercapillary distance.

TABLE 2

Requirements for the cardiac patch.

| | |
|---|---|
| Porosity | 10-100 μm |
| Patch thickness | 500 μm |
| Young's modulus | 0.2-0.5 MPa |
| Tensile strength | 3-15 KPa |
| Biodegradability | 6 months |
| Vascularization | 2400-3300 capillaries/mm2, ~20 μm intercapillary distance |

In another embodiment, the invention relates to the composition as defined above, wherein the lactone is polycaprolactone (PCL).

In another embodiment, the invention relates to the composition as defined above, wherein the copolymer of synthetic polymers is caprolactone, and L-lactide/ε-caprolactone.

In another embodiment, the invention relates to the composition as defined above, wherein the cellulose is cellulose acetyl butyrate (CAB), carboxylated cellulose or cellulose microcrystalline.

In another embodiment, the invention relates to the composition as defined above, wherein the synthetic polymer is PCL.

In another embodiment, the invention relates to the composition as defined above, wherein the natural polymer is chitosan.

In another embodiment, the invention relates to the composition as defined above, wherein the natural polymer is sodium alginate.

In another embodiment, the invention relates to the composition as defined above, wherein the self-assembling peptide is FEFEFKFK (SEQ ID NO: 1).

In another embodiment, the invention relates to the composition as defined above, wherein the support is polyurethane.

In another embodiment, the invention relates to the composition as defined above, which also comprises a plasticizer. In another embodiment, the invention relates to the composition as defined above, wherein the plasticizer is selected from tributyl citrate and acetyl tributyl citrate.

In another embodiment, the invention relates to the composition as defined above, which also comprises glass powder.

In another embodiment, the invention relates to the composition as defined above, wherein the glass powder has a diameter from 40 μm to 165 μm, preferably of 45 μm, 125 μm or 160 μm.

In another embodiment, the invention relates to the composition as defined above, which also comprises a foaming agent.

In another embodiment, the invention relates to the composition as defined above, wherein:

the concentration of the synthetic polymer is from 75% wt. to 25% wt., preferably of 25% wt.;

the concentration of natural polymer is from 60% wt. to 10% wt., preferably of 50% wt.;

the concentration of self-assembling peptide is from 4% wt. to 0% wt., preferably of 2% wt.;

the concentration of plasticizer is from 40% wt. to 0% wt., preferably of 20% wt.; and the concentration of the glass powder from 60% wt. to 20% wt., preferably of 20% wt.

In another embodiment, the invention relates to the composition as defined above, which also comprises fibers wherein said fibers are selected from polyvinylalcohol, polycaprolactone and poly(3,4-ethylenedioxythiopene poly(styrenesulfonate) or combinations thereof.

In another embodiment, the invention relates to the composition as defined above, with a thickness between 500 μm and 1000 μm; with a porous diameter between 10 μm and 250 μm; with a Young's modulus between 0.2 MPa and 0.5 Mpa; and with a tensile strength between 3 Kpa and 15 Kpa.

In another embodiment, the invention relates to the composition as defined above, with a biodegradation time of 6 months.

In another embodiment, the invention relates to the composition as defined above, which also comprises liposomes, preferably which also comprises liposomes selected from soybean-derived L-α-phosphatidylcholine.

In another embodiment, the invention relates to the composition as defined above, which also comprises at least one trophic agent, preferably wherein said trophic agent is selected from BMP (bone morphogenic protein), IGF, VEGF and platelet rich plasma (PRP).

In another embodiment, the invention relates to the composition as defined above, which also comprises at least one growth factor, wherein said growth factor is hepatocyte and/or insulin growth factor.

In another embodiment, the invention relates to the composition as defined above, which also comprises at least one drug, wherein said drug is selected from 5-azacytidine and dexametasone.

In another embodiment, the invention relates to the composition as defined above, which also comprises cells.

DETAILED DESCRIPTION OF THE INVENTION

As it was mentioned above, the present invention proposes a scaffold that is compatible with in-vitro cell seeding and cell culture to be used as vector for cellular therapy. Nevertheless as its primary action is of structural reinforcement, the device is totally compatible with a cellular therapy. Despite the present context wherein the present device is demonstrated is oriented towards CTE, the application of presented device should not be limited to curettage and cardiac transmural applications. Indeed such device can be used to soft tissue engineering such as but not limited to hernias, vein conduct. The scaffold composition comprises poly(ε-caprolactone), alginate and composite thereof with natural polymers such as chitosan, alginate fibroin. The device porosity can be tailored with a pore range of 10-250 μm, hereby permitting angiogenesis and cell seeding.

While the importance of a biomaterial to be used as a medical device for prosthetic applications, its main function in TE is to enhance cell attachment, growth and differentiation. As such, an extension of the medical device is a functionalization with cell signaling agent capacity. The device proposed by the present invention can be functionalized with a biocompatible and biodegradable self-assembled gel. Whilst it functionalization is not necessary for the medical device to ensure its primary actuation as it is foreseen to provide the scaffold an ECM-like micro-environment, the polymeric self-assembled structure, that is composed of but not limited to peptidic or polyurethane amphiphiles, can be loaded with chemical and biological cues via entrapment method or covalently. Such cues can either be exogeneous or being PRP. Should PRP be selected, the medical device would remain a medical device and shall not fall under drug regulation.

To initiate regeneration of the host tissue, it is essential that the biomaterial encourages in-vivo revasularization as well as favours integration with the host tissue. At the same time, it should degrade at a predefined rate to enable its replacement with newly formed tissue by safely degrading at a similar rate of the new tissue formation and eventually removed from the body by natural metabolic pathways without producing toxic by-products.

The basic requirements for myocardial bioengineered constructs include robust yet flexible mechanical properties, ability to withstand contraction, electro-physiological stability and vascularization ability. In fact if it is expected that the patch will provide a temporary mechanical support to the infarcted myocardium in order to prevent negative effects on the spare tissue and to prevent aneurism formation in the infarcted area, while the regenerative processes take place. We proposed a cardiac patch adequate for both curettage and transmural application.

From the aforementioned critical review regarding existing solution for cardiac patch application, the present invention provides a cardiac patch end product based on polymeric scaffold structure of tailorable porosity and dimension/a drug delivery system/a functionalisable gel garnished with a stitch resistant biocompatible and biodegradable film support (FIG. 1).

Applications foreseen are curettage, mechanical support, pericardium contension and transmural application.

This 4 elements system is proposed as a medical device for structural reinforcement purposes. The polymeric structure is immobilized onto the film support in an adhesive less manner.

Electrospun fibers based drug delivery system is immobilized onto the film free side of the polymeric scaffold. The gel element can be immobilized onto the aforementioned architecture by impregnation, centrifugation and gravimetrically. The present statement refers to the application of a medical device for myocardial infarct treatment.

The application is foreseen for both in-vitro and in-vivo application. The drug delivery system is introduced for its complementarity with gel element of the device. Both parts of the device can be loaded with cell signaling agent, drugs for research and use. In the perspective of in-vivo application, the fiber based drug delivery system can be foreseen as a direct tool for gel functionalisation with patient blood components.

Inherent characteristics: The proposed cardiac patch is a medical device that provides structural support to the pericardium and myocardium tissues. The 4 components system mechanical properties matches those of the tissue to be replaced. The 3D hydrophobic/hydrophilic scaffold component provide a mechanical support to a gel that acts as scaffold plasticizer and provide an hydrophilic interface with the host environment. The gel can be easily functionalized with the cell signaling agent by entrapment. The gel can also collect from its immediate environment cell signaling agents. Electrospun fibers based drug delivery system can be used as a complementary tool to the gel for device loading with cell signaling agents, drugs, etc. The electrospun fibers can be used as an intrinsic element gel functionalization for in-vivo and in-vitro application. All components of the proposed cardiac patch are compatible accordingly to 10993:5 and biocompatible with cardiac and bone marrow progenitor cells.

EXAMPLES

Example 1

Natural Polymers/Plasticizers and PCL and Derivatives Thereof/Natural Polymers/Plasticizers Thick and Porous Materials It has been defined different strategies for the development of PCL based hybrids scaffolds of tailorable thickness and porosity, production from which scaffolds should be easily amenable to mass production perspective. As presented in FIG. 2 processing routes were investigated and compatible polymeric solutions were studied.

Among the approaches and the different studied polymeric systems, salt leaching and solvent casting did not provide adequate solutions for highly porous system. Indeed in both cases studies based on a selection of aqueous or organic solvent soluble porogen and FDA approved blowing agents have led to an unsatisfactory porosity.

On the other hand composite structures compatible with roll to roll technology of tailorable thickness and porosity have been achieved by melt processing (FIG. 3).

The nature of thermo-calorimetric behaviour of the polymers clearly dictates the selection of the system. For example, PCL is a thermo setting polymer of low glass temperature transition and therefore can be treated/processed by melt pressing at conditions compatibles with hybrids conditions. On the contrary cannot be processed by this technique.

By virtue of the end product constraint, focus was therefore drawn towards the melting and press approach and thermoplastic polymers were used for such design (FIG. 4)

Plasticizers were necessary to be introduced in such compositions due to the natural stiffness of the natural polymers and resulting hybrids. All the plasticizers used in the present work have been reported in the literature for biomaterial applications and are FDA approved. The effect of plasticizers onto the mechanical properties of the scaffold matrices were measured as exemplified in FIG. 6.

Blowing agents and glass beds (FIG. 7 and FIG. 8) were studied as pore generating agents.

Mixtures were prepared employing different combinations of natural and synthetic polymers and plasticizers (Table 3).

TABLE 3

Composition patches

| COMPONENT | ROLE | AMOUNT (% wt.) | TOLERANCE (% wt.) |
|---|---|---|---|
| COMPOSITION PATCHES PREPARED BY MELTING BLENDING | | | |
| PCL (or Lactide-εCaprolactone) | Synthetic polymer | 50 | ±25 |
| Chitosan, sodium alginate or CAB | Natural polymer | 35 | ±25 |
| Tributyl citrate or acetyl tributyl citrate | Plasticizer | 20 | ±20 |
| Glass powder (less than 160 microns) | Porogen agent | 40 | ±20 |
| Sodium bicarbonate | Blowing agent | 4 | ±4 |
| Self-assembled peptide | Drug delivery system | 2 | ±2 |
| COMPOSITION PATCHES PREPARED BY CASTING AND DRYING | | | |
| PCL (or Lactide-εCaprolactone) | Synthetic polymer | 50 | ±25 |

TABLE 3-continued

Composition patches

| COMPONENT | ROLE | AMOUNT (% wt.) | TOLERANCE (% wt.) |
|---|---|---|---|
| Chitosan, sodium alginate or CAB | Natural polymer | 35 | ±25 |
| Tributyl citrate or acetyl tributyl citrate | Plasticizer | 20 | ±20 |
| Bioglass S53P4 | Vascularization agent | 40 | ±20 |
| Self-assembled Peptide | Drug delivery system | 2 | ±2 |

The strategies carried out to select the most suitable components for the patches are presented in FIG. 5.

Patches with the synthetic polymers (PCL, L-lactide/ε-caprolactone copolymer), the natural polymer (sodium salt of alginate, chitosan, CAB) and the plasticizer tributyl citrate were prepared.

Such materials were then characterized by molecular spectroscopy and calorimetrically (FIG. 9). Modification of melting point (Tm) crystalline polymer with other polymers provides information about their miscibility. Pure PCL employed for this work presents a melting point of 60.8° C. Introduction of plasticizers, natural polymer and glass could affect melting point of PCL. PCL can interact with natural polymers via hydrogen bondings.

Although the initial work was focused on polymer melting processing and further treatment with hydrofluoric acid to obtain highly porous three-dimensional scaffolds other strategies such as freeze drying and phase inversion process have been studied.

For this process the composition blends were dissolved or dispersed (in the case of chitosan and the glass powder) in dimethylsulphoxide, which presents a relatively high freezing point (18.5° C.). The studied components for the scaffolds were: PCL and L-lactide/ε-caprolactone as synthetic polymers, chitosan as natural polymer and bioglass S53P4 with size less than 45 microns as pore generating agent.

Advantages and drawbacks of both processing techniques (melting processing and phase inversion) are summarized in Table 4.

TABLE 4

Advantages and drawbacks of selected scaffold processing techniques.

| Processing Technique | Advantages | Drawbacks |
|---|---|---|
| MELTING PROCESSING + HF TREATMENT | 1.- No solvent<br>2.-Introduction of additives<br>3.-Easy mass production of thick and thin scaffolds<br>4.- Surface porosity: larger pores<br>5.- Tailorable porosity | 1.- hydrofluoric acid (HF) treatment |
| FREEZE/PHASE INVERSION | 1.- No HF treatment<br>2.- Tailorable thickness<br>3.-Easier industrial implantation | 1.- Surface porosity: smaller pores |

The study of surface porosity by SEM shows that samples prepared by phase inversion presents smaller pores (around 20 microns) than the melt processed ones (dimensions 50 microns). Moreover, porosity in melting processing samples can be controlled by the size of used glass powder (see FIG. 10).

The mechanical properties of patches prepared by phase inversions show to be with suitable elasticity (191% for PCL and 257% for and copolymer L-lactide/ε-caprolactone patches) and tensile strength for cardiac patch application (see FIG. 11).

Example 2

PCL/Natural Polymers (Chitosan, Cellulose acetyl butyrate, alginic acid)/SEQ ID NO: 1 (FEFEFKFK) (PERA-UniMa-PPI)

In order to facilitate CP end product production and acceptability by the end user, a multi layered architecture where laminas of distinctive but complementary materials have been proposed, where a biocompatible elastomer such as but not limited to polyurethane serves as a base to a thick porous scaffold composed of but not limited to composites of poly(ε-caprolactone) with natural polymers such as but not limited to alginate and chitosan. While the micro and macro structural features are compatible with angiogenesis, cell seding, cross-structural nutrient transport, a self-assembled peptide is used to coat this central element to provide an ECM like feature to the device. Device functionalization with chemical and biological cues is achieved through the functionalisation such assemble assembly of peptides. The structure permits the instauration of concentration gradient thereby, facilitating cell differentiation, expansion and proliferation.

A stichable or sewable medical device will be composed of 3 elements: a melt pressed, freeze-thawn, freeze-dried scaffold with impregnated or supporting a self-assemble polypeptide gel. In such configuration, the synthetic-natural polymer will provide a support for an easily functionalisable peptidic gels. The argument relies on the easy chemical and biological cue entrapment within a gel allied to a synthetic structure of mechanical properties. While such edifice should be place in lieu of the scar tissue for host tissue regeneration therapy, a biocompatible and biodegradable polyurethane support is used to immobilise the patch onto the cardiovascular tissue (FIG. 12).

Among all the evaluated combinations, best results are obtained with composite structures of low surface charges (low chitosan or alginic acid content) or with neutral polymers such as the PCL/Cellulose acetyl butyrate (FIG. 13)

Scaffolds prepared as aforementioned are the base of three components patch concept. Components beside scaffold are polyurethane layer for sewing of patch, scaffold and gel for release of growth factor or other possible entrapped agents. These entrapped agents could be but are not limited to:

Bioactive molecules promoting stem cell recruitment, adhesion, proliferation and differentiation: IGF-1 (insulin-like growth factor-1), HGF (hepatocyte growth factor), 5-azacytidine, etc.

Bioactive molecules promoting angiogenesis: VEGF-A (vascular endothelial growth factor A), HGF.

Plasma Enriched Platelets can also been prepared from patient own blood components and entrapped within the gel formulation so as to provide a medical device functionalised with endogeneous chemical and biological cues.

FIG. 14 shows a schematic representation of three components patch concept. In the following examples (Example 3 and 4) the development of three components system is presented The device can be further functionalized with drug delivery system such as but not limited to poly(ε-caprolactone), and composites thereof where natural polymers are second component of the formulated drug delivery device (FIG. 15).

Example 3

Preparation of Cardiac Patch

To facilitate the suture of cardiac patch, polyurethane sewable support was immobilized onto PCL based scaffolds. FIG. 16 represent step by step procedure for the preparation of stitchable cardiac patch.

Example 4

Functionalization of Patches

Polypeptide Impregnation

Self assembled peptide such as but not limited to FEFEFKFK (SEQ ID NO: 1) polypeptide gel have been immobilized onto/into into PCL/chitosan, PCL/alginate and PCL/cellulose acetyl butyrate (CAB) patches. Gels of polypeptides were introduced in the patches by centrifugation and heating. These can also be applied by lamination with wire bar or application blade application technique. Chromatography analysis reveals that all patches tested contains polypeptides. Gel content of patches does not depend on the preparation method or the gel concentration. It depends on the scaffold porosity and natural polymer structure. Best results were obtained for neutral polymers such as CAB (FIG. 13)

Polyurethane Gel Impregnation Two types of polyurethane gel are prepared:
  Physical crosslinked gel: after 24 hours in water increase its volume 20-25 times.
  Thermoreversible gel: polyurethane hydrogel with low LCST (lower critical solution temperature) and a gelification time of 62 seconds at 28° C.

PU hydrogel absorption in scaffolds has been measured. This value goes from 0.5% wt. to 5.70% wt depending on porosity and composition of scaffold and porosity of polyurethane immobilized layer.

Electrospun Functionalized Nanofibres

Besides gel impregnation, functionalized fibers have been introduced in the patches for topical drug/trophic agent release (4 components system: polyurethane layer, biopolymer patch, electrospun fibers based drug delivery system and a functionalisable self-assembling peptide). Introduction of fibers could also be a vehicle to load the patches with cell signaling agents or grow factors. has deposited electro spun fibres onto polycaprolactone patches by coaxial electro spinning technique (FIG. 17).

Coaxial electrospinning technique allows preparing the core of the nano-fiber with one material and the shell with a different one. Using this technique, liposomes and growth factors were encapsulated in the core of the fibre in a PVA solution and the shell of the fibre was made of PCL. Drug profile of growth factors entrapped in coaxially electrospun fibers has been determined. These nanofibers showed good adhesion to the material and were suitable for further use in combination with bioactive substances. According to the results coaxial electro-spinning seems adequate for functionalization of scaffold. Moreover this technique allows the gel immobilization.

Example 5

Characterisation

Swelling Test

PCL does not show a significant swelling in water or cell mediums such as phosphate buffered saline medium (PBS) due to the hydrophobic nature of this polymer. Blends of PCL with natural polymers present swelling in PBS. PCL/CAB blends, increasing of CAB produce higher swelling: up to 10-12.5% for sample with 30 w % PCL (FIG. 18).

The swelling in PBS of L-lactide/-caprolactone copolymer blends has been studied. Copolymer/chitosan blends presents more swelling than PCL due to higher hydrophilicity of L-lactide/ε-caprolactone. Blends with percentage of 20% chitosan presents 16% weight gain for PCL blend and until 42% for L-lactide/ε-caprolactone (FIG. 19).

Example 6

Biological Evaluation

Biodegradation/Biocompatibility (Long Term Toxicity) Tests

Tests were carried out in accordance with the supplied protocol.

Protocol: The in vitro degradation properties were evaluated in three different solutions:
  phosphate buffer solution (PBS);
  cell culture medium, composed by Dulbecco's modified Eagle's medium with high glucose, 10% fetal bovine serum, 2 mM glutamine, penicillin (100 U/ml) and streptomycin (100 µg/ml);
  PBS with collagenase (16 U/ml).

Scaffolds weight losses during degradation are measured by changes in dry weight after incubation for specified time periods. All the experiments should be done in triplicates; the results are the mean (±SE) of three determinations.

1) Materials samples, cut into squares of 1 cm², are dried in oven at 37° C. up to constant weight;
2) The starting dry weight, $W_0$, is determined for each sample;
3) Samples are introduced in 10 ml of solution and maintained into an agitating bath at 37° C. for specified time periods (e.g. 1, 3, 7, 14, 21, 30, 45, 60 . . . days);
4) At appointed times, samples are removed from solution, rinsed in bi-distilled water and dried in oven at 37° C. up to constant weight;
5) The dry weight at time t of degradation, $W_t$, is determined for each sample;
6) Percentage weight loss is evaluated according to the following equation: $(W_o-W_t)/W_o \times 100$.

In some cases, the following additional aspects were taken into consideration:
  Quantitative determination of the degradation products, using HPLC or UV methods;
  Physicochemical characterization of the degradation products, as well as the degraded samples, through FT-IR, DSC, GPC;
  Variations of pH in the degradation solution.

Said protocol has been used with the following modifications: (1) in order to increase the surface area, samples were cut at 3 cm squared (3 cm2); (2) in order to improve the drying process, samples were dried at 45 deg. C.; (3) in order to prevent microbial contamination, samples were sterilized by dipping them in ethanol at each sampling time for about 30 seconds and dried in air to remove excess ethanol; and (4) pH variations have been monitored. Test were carried out in phosphate saline buffer (PBS), Dulbecco's Modified Eagle Medium DMEM and PBS/Collagenase.

(PCL or L-lactide/-caprolactone) alginic acid based cardiac patch did lead to any pH change.

Cytotoxicity tests have been carried out by the University of Pisa. Additionally cell culture tests were also performed. FIG. 20 represents rCPC (Rat Cardiac Progenitor Cells) and BMC (Bone Marrow Progenitor Cells) cell culture after 7 days of culture supporting short and long term non-toxicity of (PCL or L-lactide/-caprolactone) alginic acid based cardiac patch.

Cell Seeding Culture Test of the Poly(ε-Caprolactone): Chitosan Scaffold Device poly(ε-caprolactone):chitosan was seeded with rat aortic endothelial cells (rAoECs) and rat cardiac cell progenitors (rCPCs), $45 \cdot 10^3$ cells/cm$^2$ respectively. FIGS. 21 and 22 represent cell survival under long term and chronic toxicity biological evaluation. The results show that the scaffold supports and promotes proliferation of rAoECs and rCPCs (FIG. 23).

Example 7

In-Vivo Studies

The seeded polyurethane(support)/poly(ε-caprolactone):chitosan base structure of the cardiac patch were implanted in vivo and sutured onto the on the Left Ventricular (LV) free wall after cryoinjury on the rat heart (FIG. 24).

At day of implant +4 and +10 days respectively, the animal was sacrificed for immunohistochemical analysis.

FIG. 25 demonstrates the stability of the proposed device post sacrifice.

FIGS. 26 and 27 demonstrate the adequatness of the device for soft tissue structural support/acellular therapy (FIG. 26), cellular therapy without being associated to any inflammatory process.

From FIG. 27, in-vitro data support static biological evaluation, which qualified the scaffold material as non-toxic and able to support stem cell culture. Furthermore, this supports the claims of the proposed device:

a. provide a structural support to the damage tissue b. can be used with cellular and cell sheet therapy.

c. Cells seeded onto the scaffold can be expanded in vitro and implanted in-vivo. As migration occurs in-wards towards the zone of the lesion, the proposed scaffold is also adequate for transmural applications.

Example 8

Mechanical Properties

Mechanical properties of the cardiac patches have been determined as a function of natural polymer content in dry and wet conditions showing the adequate mechanical properties of the proposed polymeric scaffolds (Table 4)

TABLE 4 the tensile properties of selected PCL and L-lactide/-caprolactone based cardiac patches.

| Inmersion Time In PBS (hours) | ELASTIC MODULUS (MPa) Sample: L-lactide-εcaprolactone/chitosan/TBC/glass (125-160 μm)/NaHCO$_3$ treated 10 min HF | ELASTIC MODULUS (MPa) Sample: PCL/chitosan/TBC/glass (125-160 μm)/NaHCO$_3$ treated 10 min HF |
|---|---|---|
| 0 | 13.14 ± 1.41 | 31.94 ± 8.35 |
| 48 | 4.40 ± 2.22 | 28.19 ± 2.84 |
| 120 | 5.04 ± 1.53 | 44.44 ± 58.63 |

A) (■) PCL+10% CAB, (●) PCL+20% CAB, (▲) PCL+ 30% CAB. Three blend series were prepared with 20% tributyl citrate, 10% glass powder 125 microns, 10% glass powder 160 microns and 3% NaHCO3 and then treated with HF during 10 minutes.

B) (■) PCL+10% CAB, (●) PCL+20% CAB, (▲) PCL+ 30% CAB. Three blend series were prepared with 20% tributyl citrate, 20% glass powder 125 microns, 20% glass powder 160 microns and 3% NaHCO3 and then treated with HF during 10 minutes.

Figure 1:
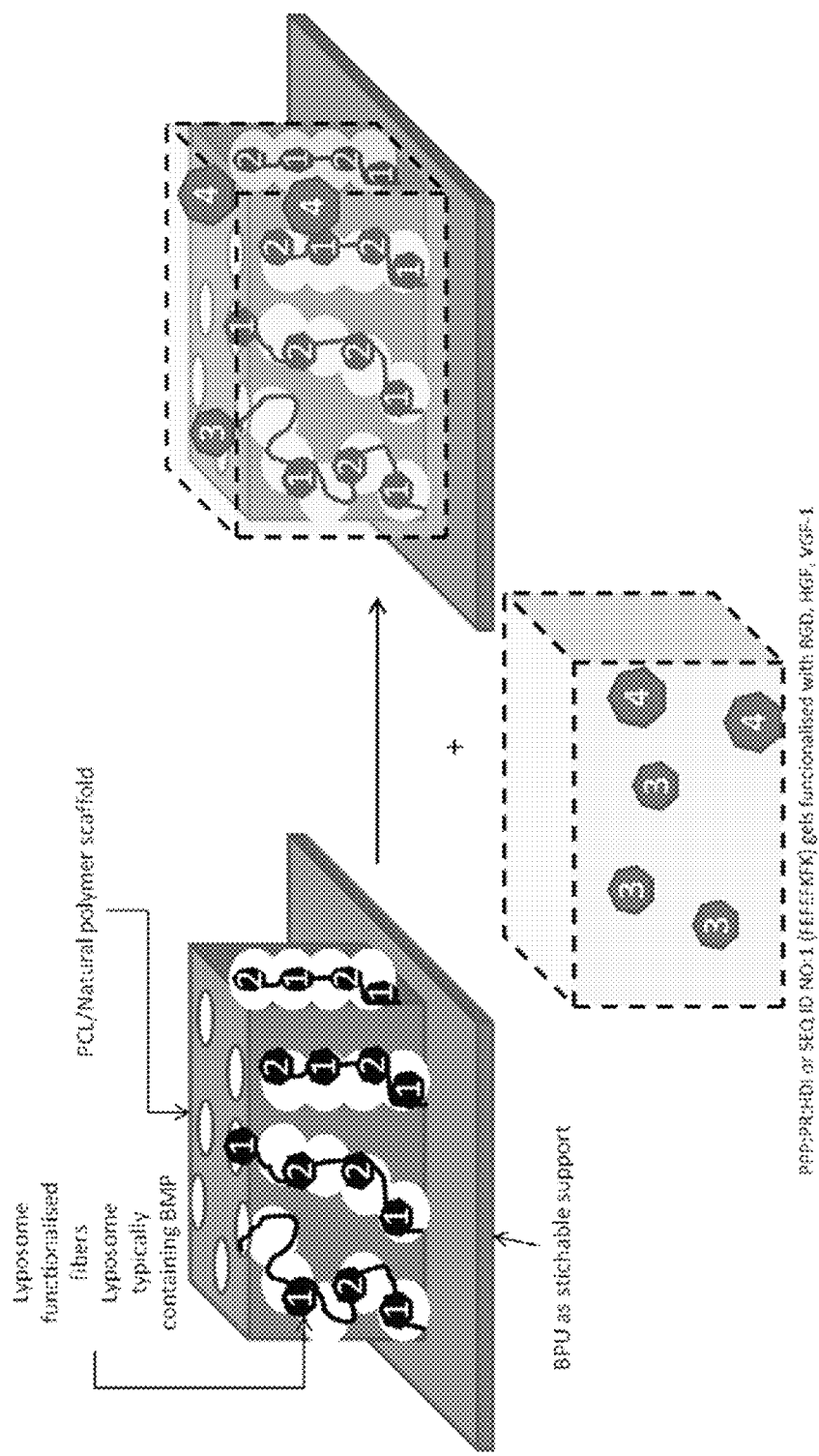
FIG. 1: Schematic representation of Cardiac Patch medical device
Figure 1:
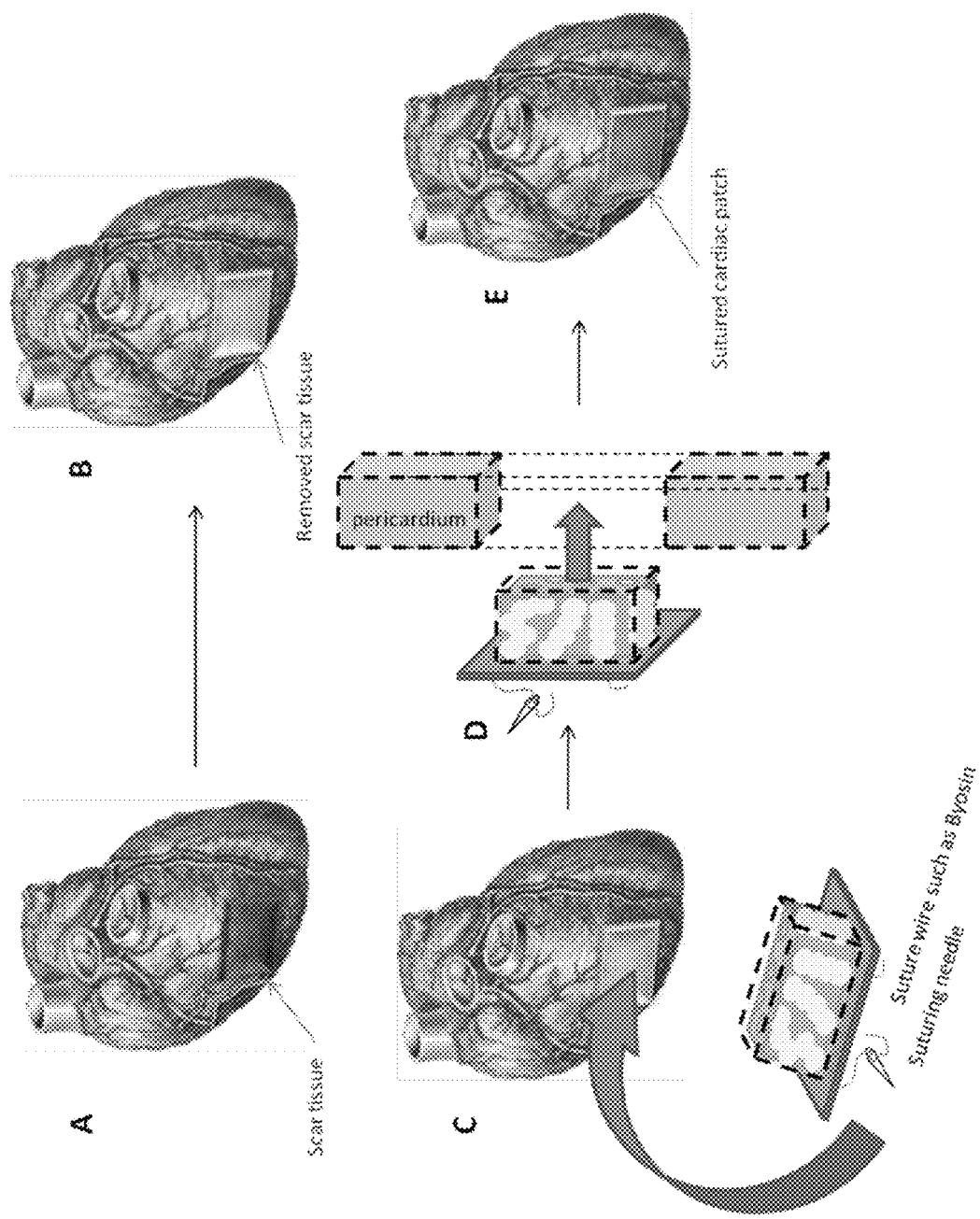
Figure 2:
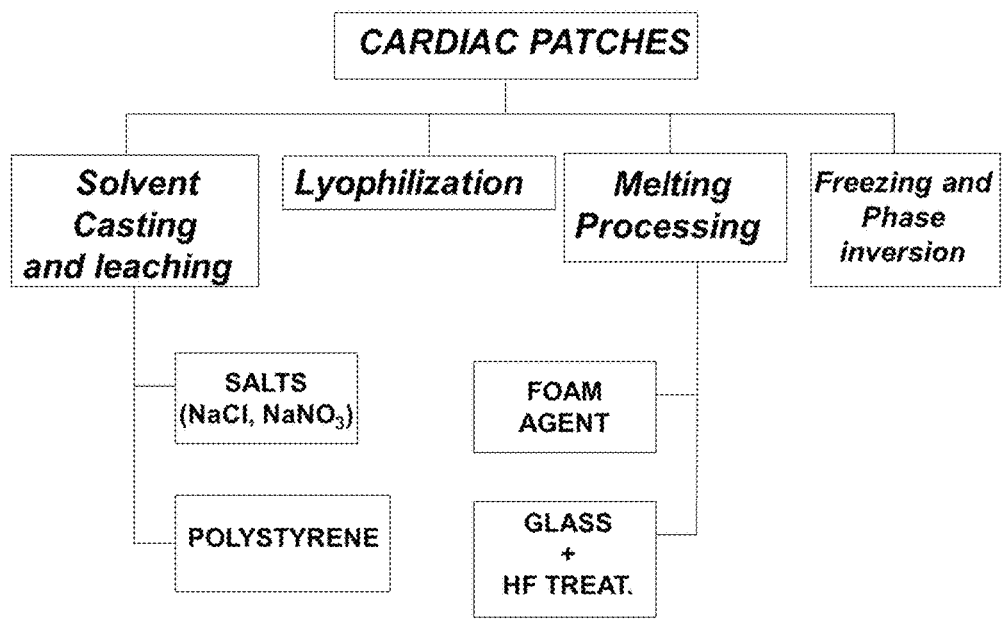
FIG. 2: Polymer processing technologies studied for the production of size and porosity controllable biocompatible and biodegradable polymers for cardiac patch applications FIG. 3 Selected examples of scaffolds obtained from PCL and PVA composites by A) solvent casting/particle leaching; B) lyophilisation and C) melt press approach.
Figure 3:
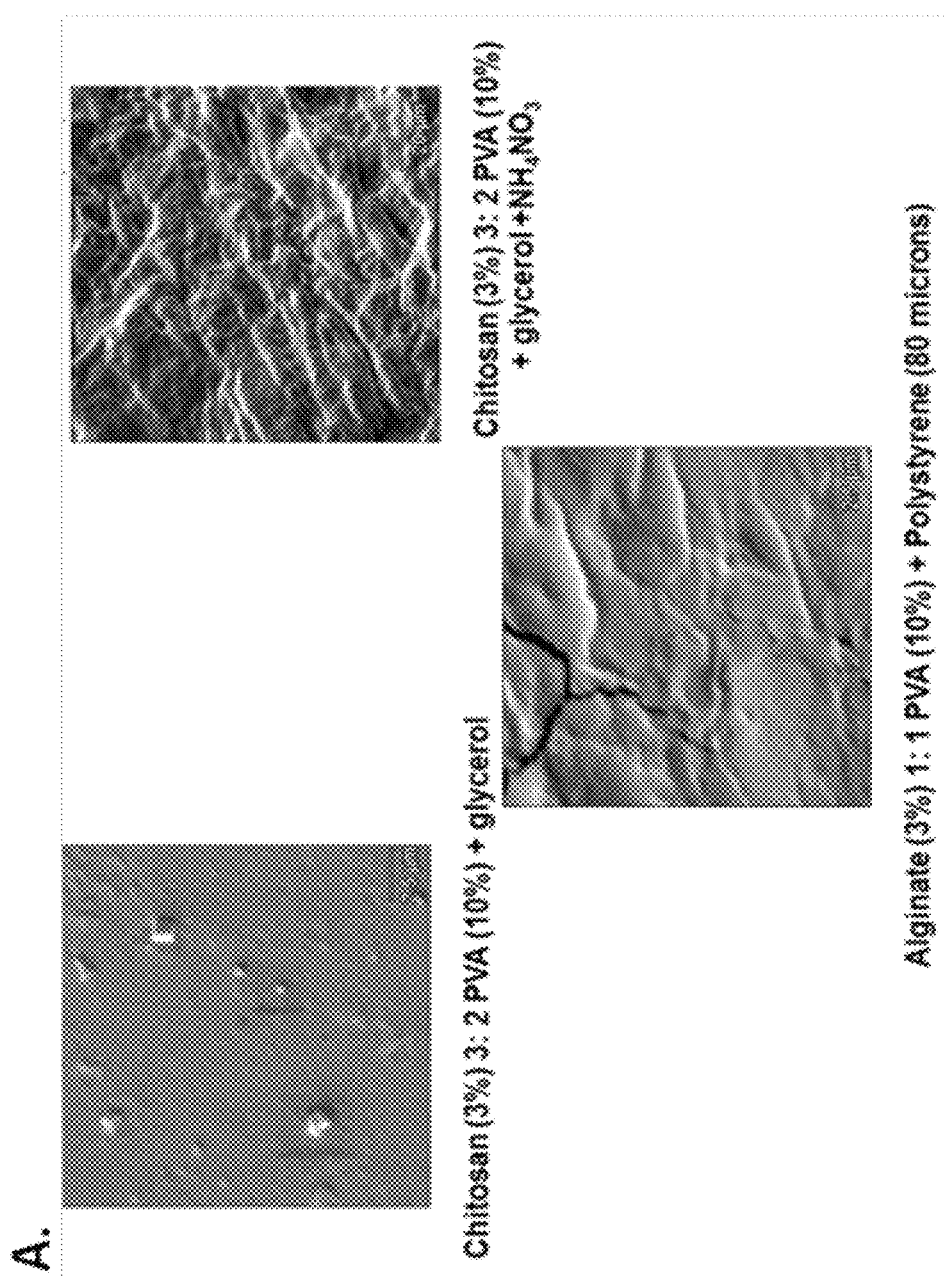
Figure 3:
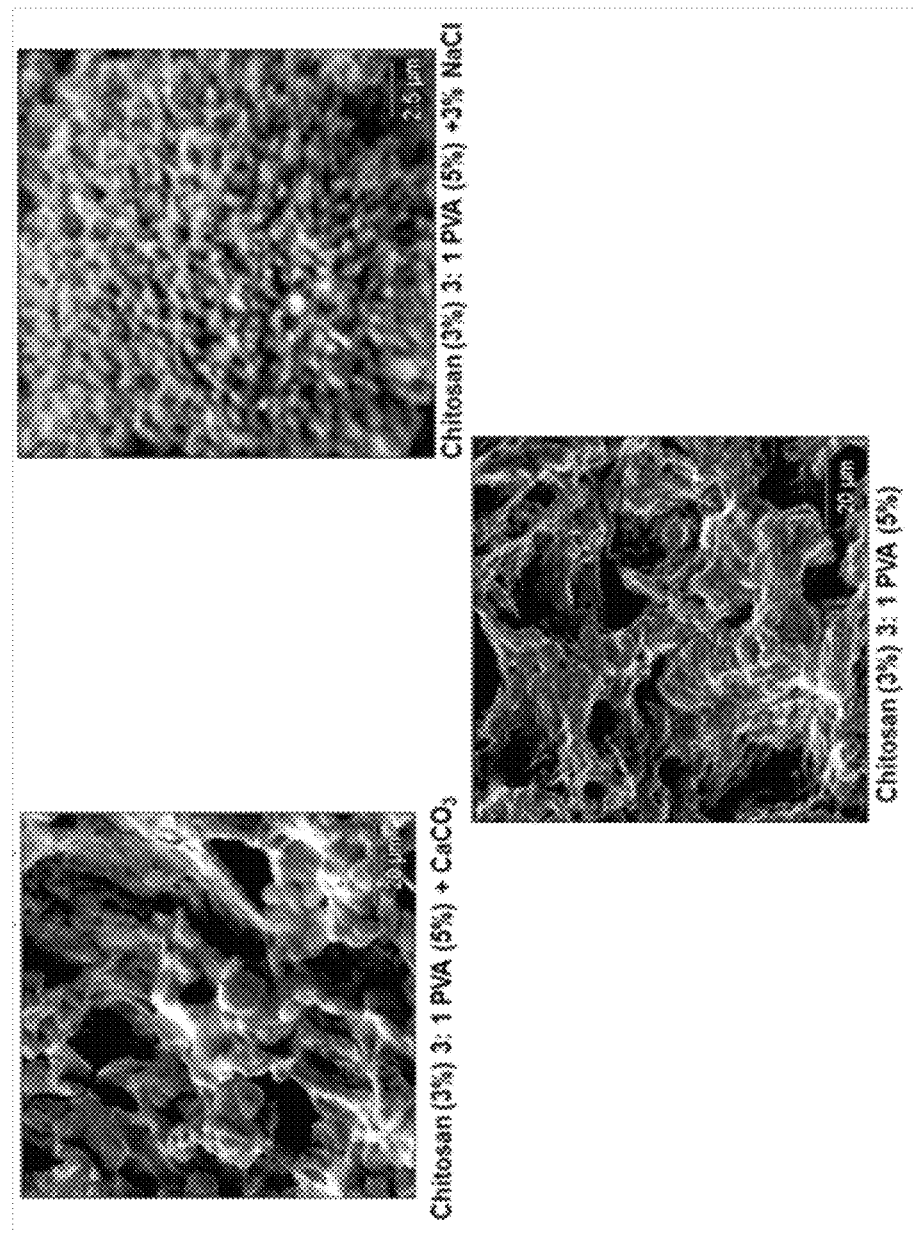
Figure 3:
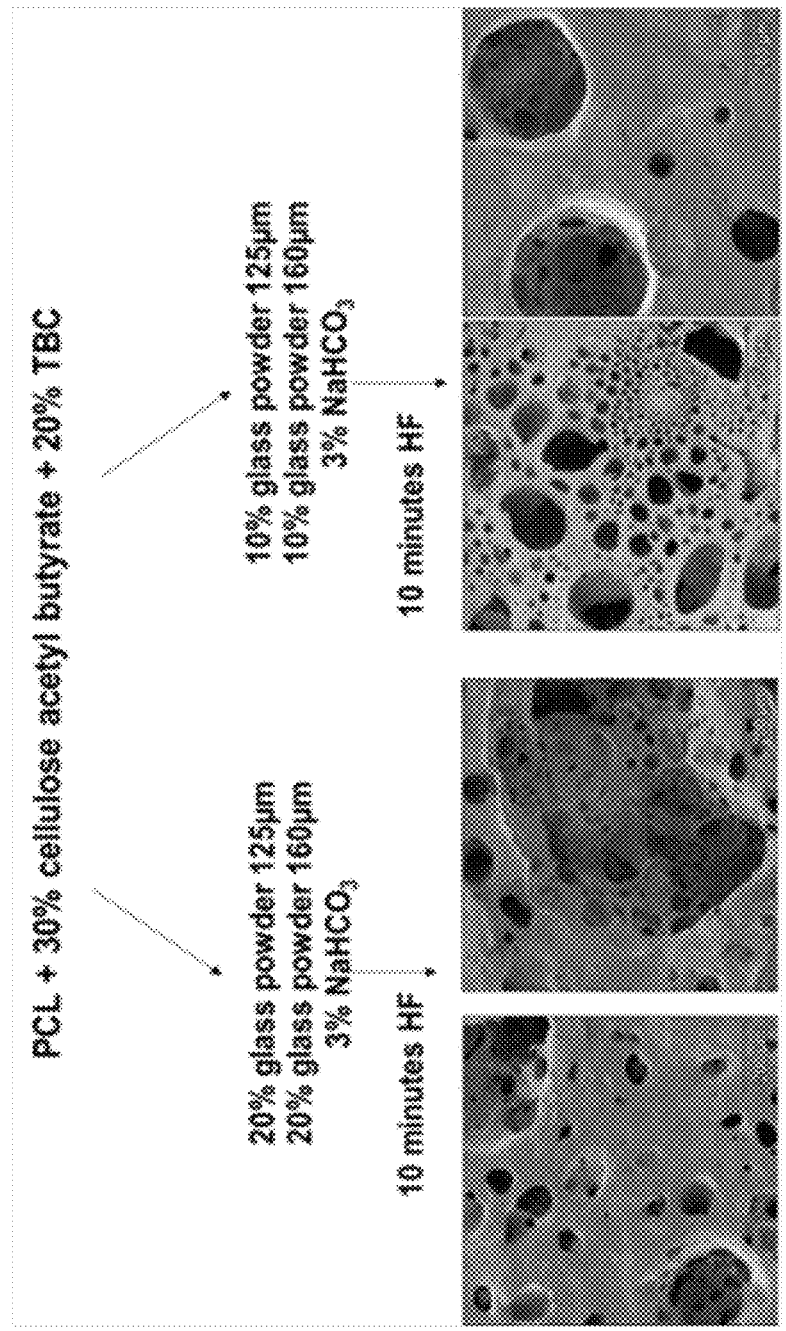
Figure 4:
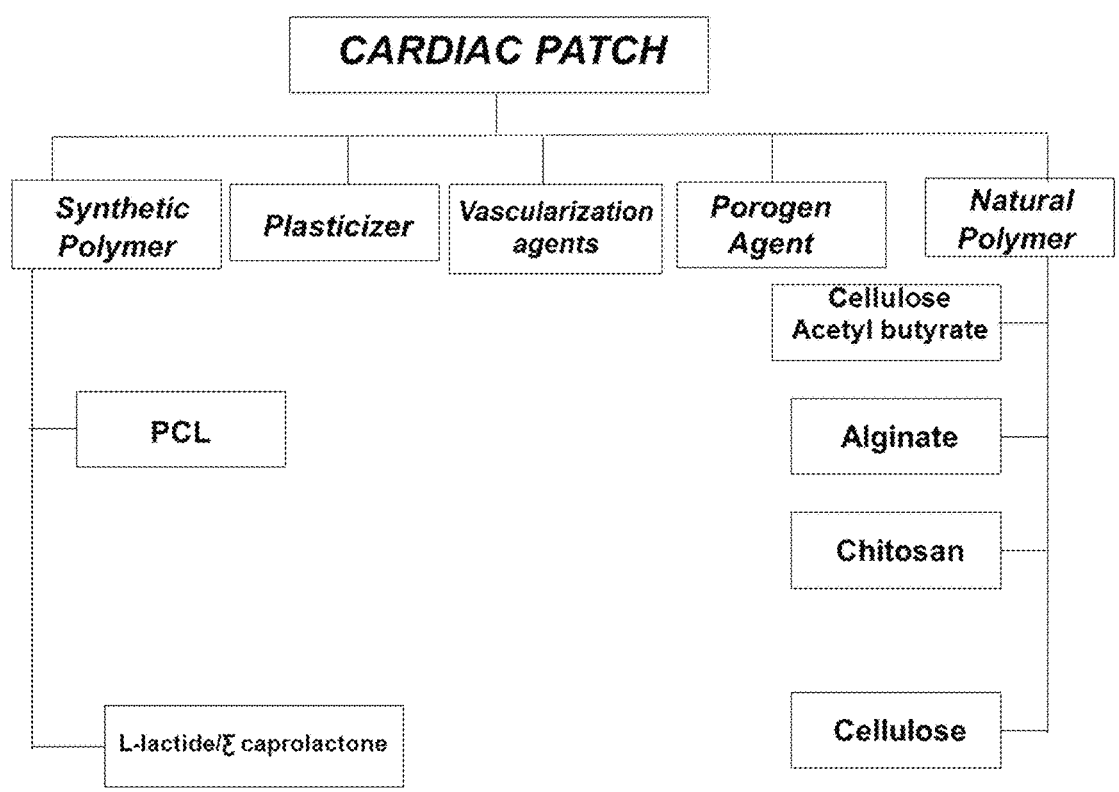
FIG. 4: schematic representation of the Cardiac Patch compositions
Figure 5:
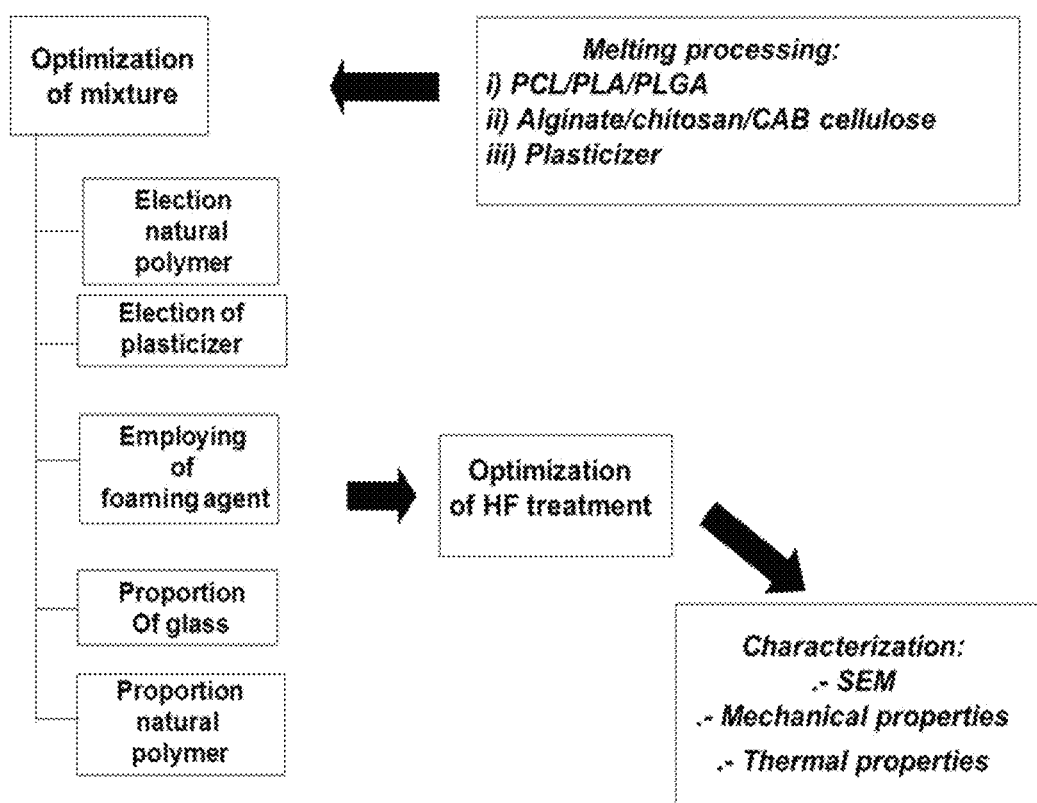
FIG. 5: Schematic representation of chronological experimental work carried out for patches preparation
Figure 6:
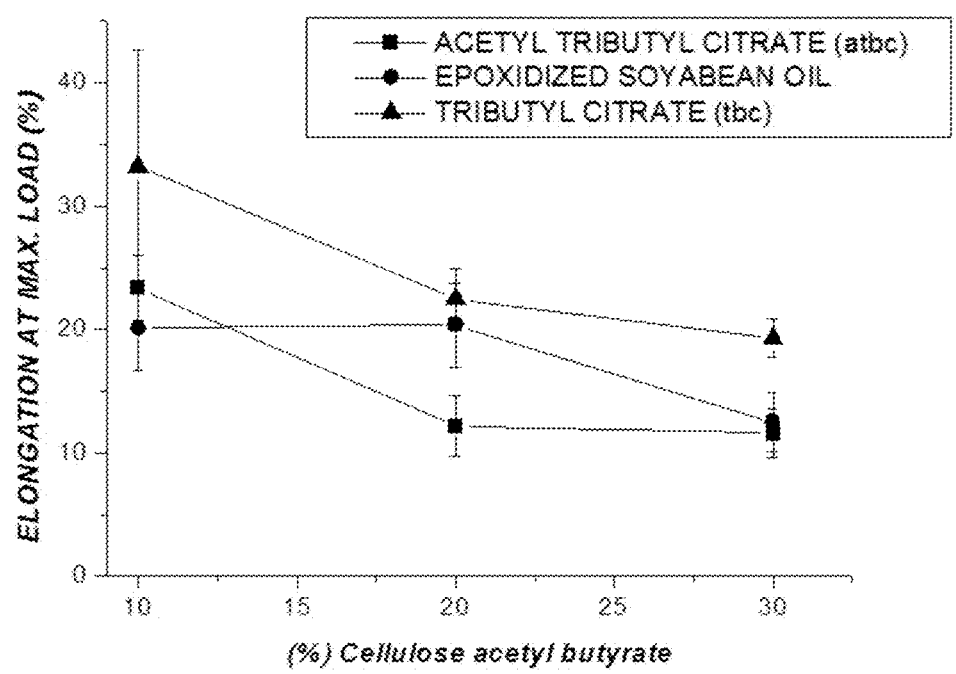
FIG. 6: Elongation at maximum load of patches with different concentrations of CAB and plasticizers: acetyl tributyl citrate, epoxidized soybean oil and tributyl citrate.
Figure 7:
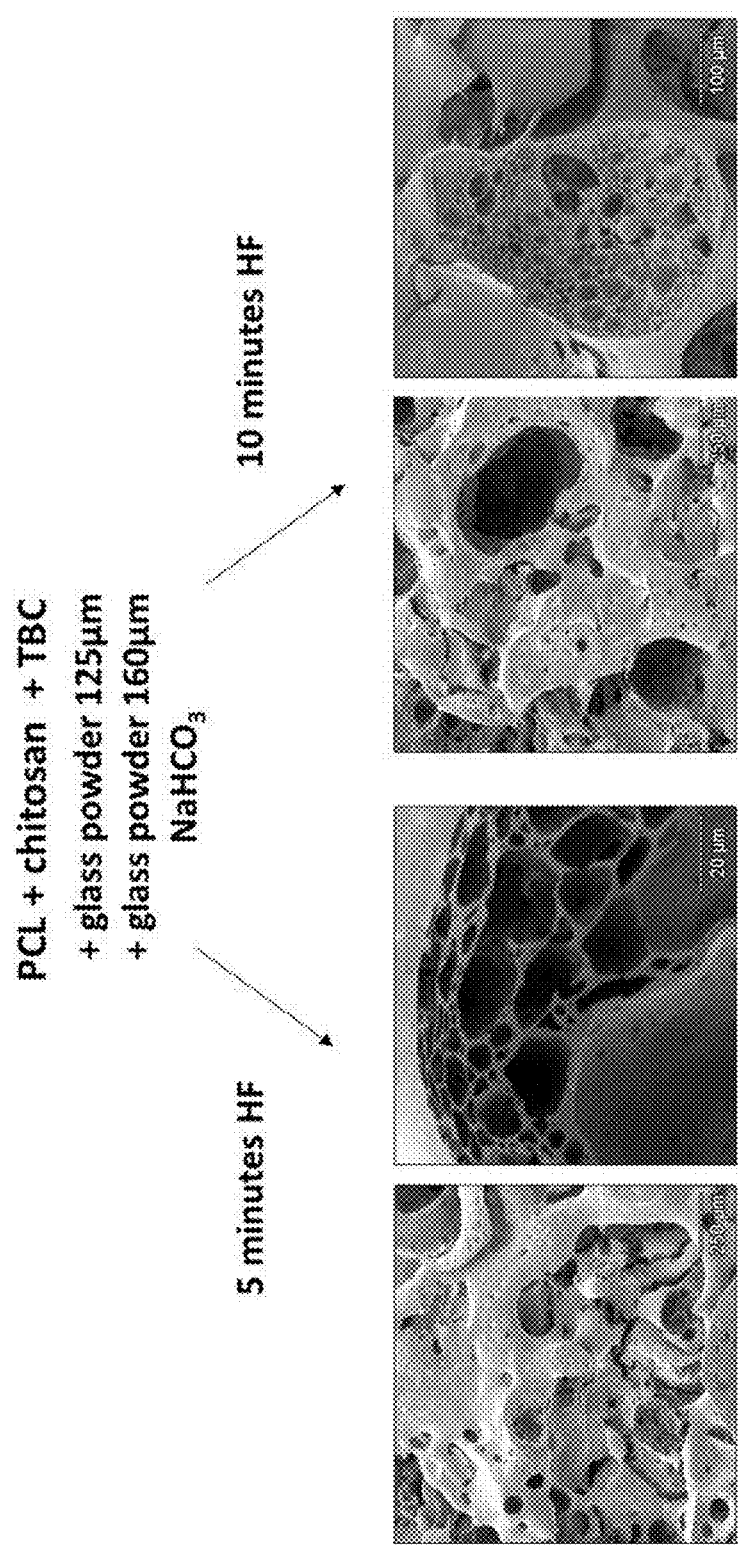
FIG. 7: SEM photographs of PCL+chitosan+glass patches treated 5 and 10 minutes with hydrofluoric acid.
Figure 8:
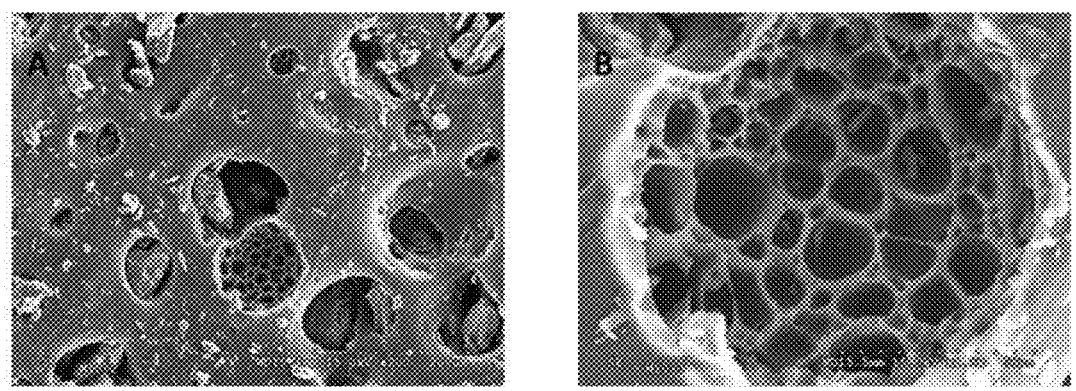
FIG. 8: SEM photographs of PCL/cellulose/TBC/glass powder (diameters of 125 μm and 160 μm)/NaHCO$_3$ patches treated with hydrofluoric acid.
Figure 9:
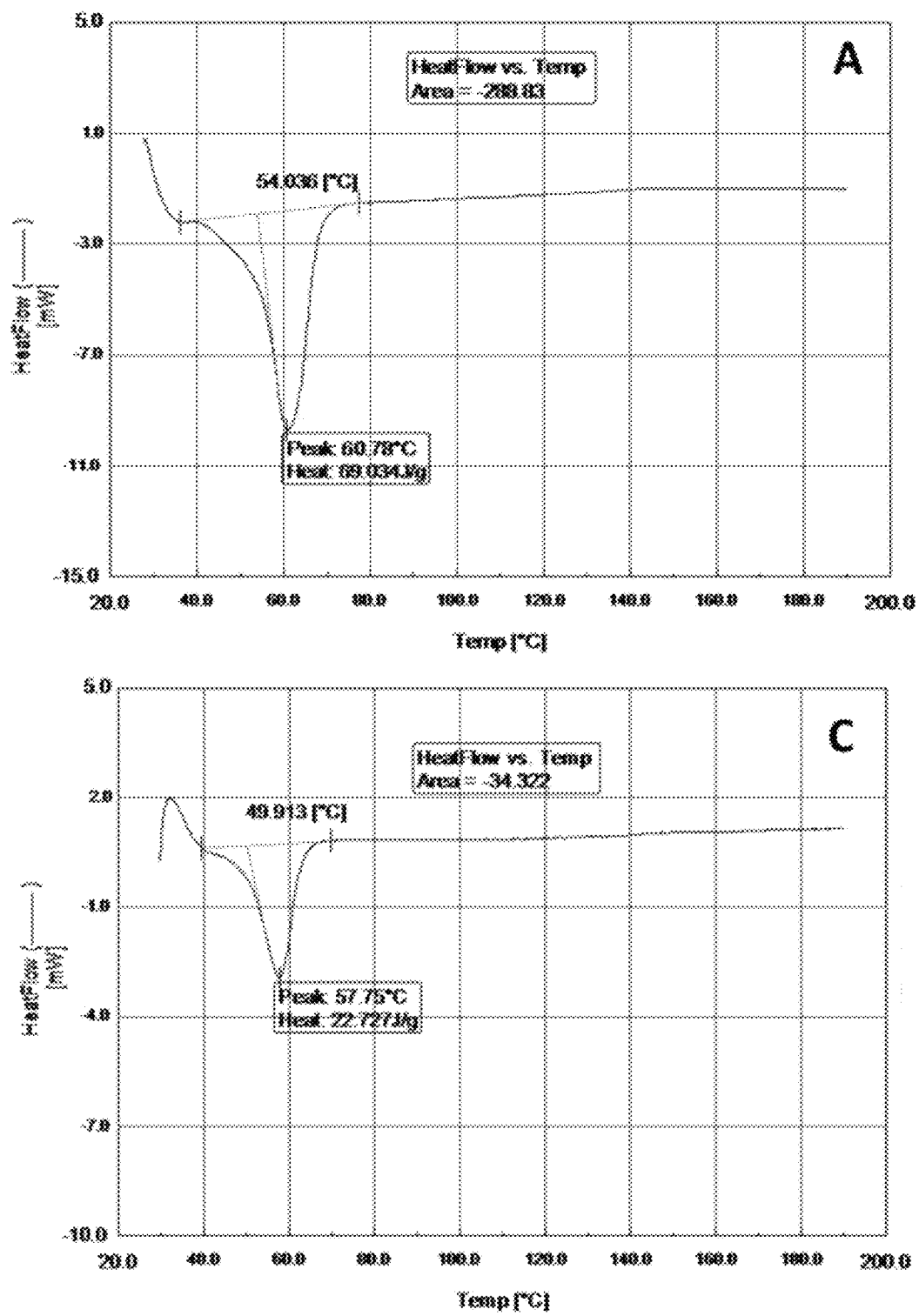
FIG. 9: DSC thermograms of A) PCL pure; B) PCL+30% chitosan 30%, C) PCL+40% chitosan and D) PCL+60% chitosan. Blends B, C and D are prepared with tributyl citrate/glass powder (125 and 160 microns particle size)/NaHCO3 without treatment.
Figure 9:
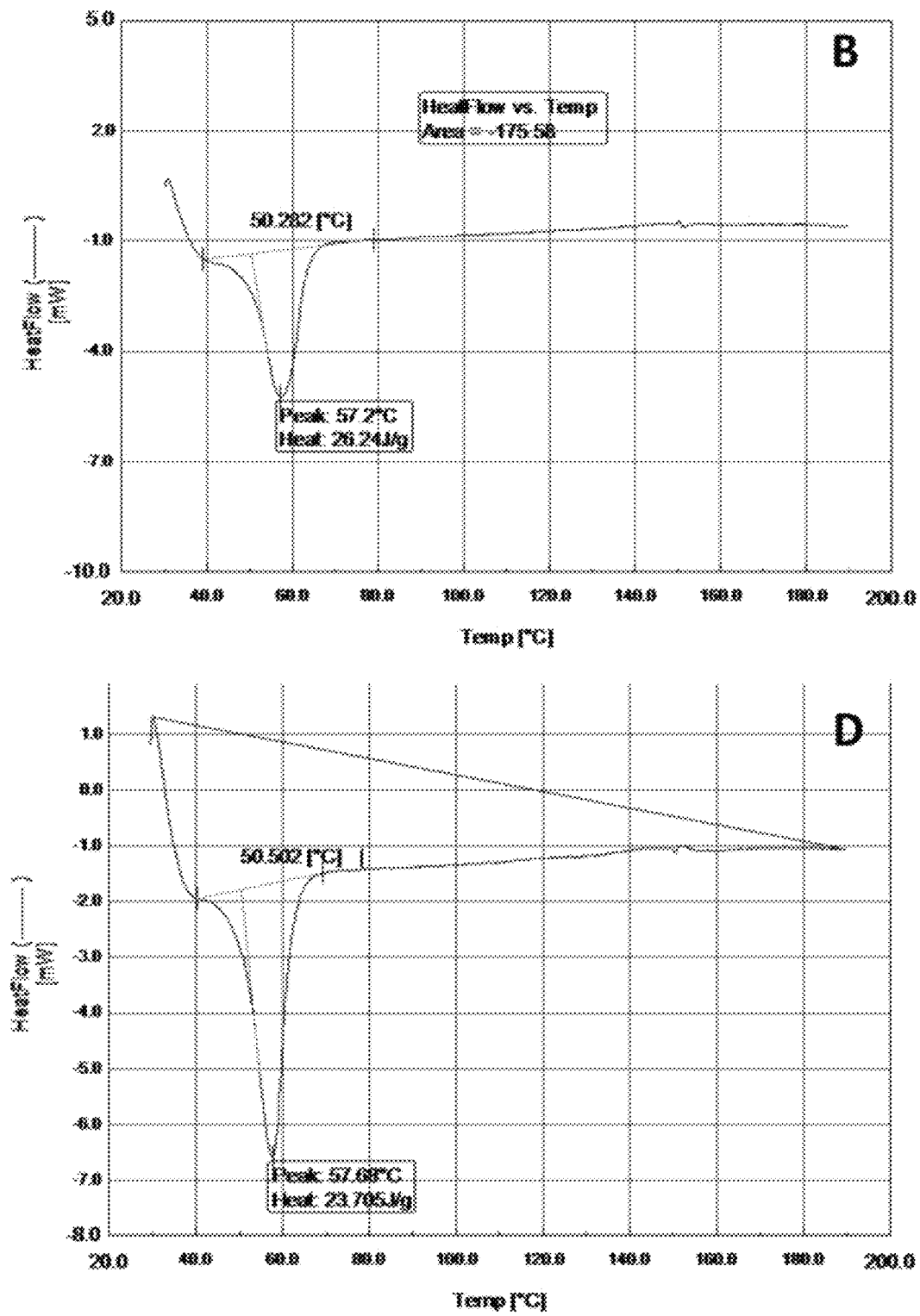
Figure 10:
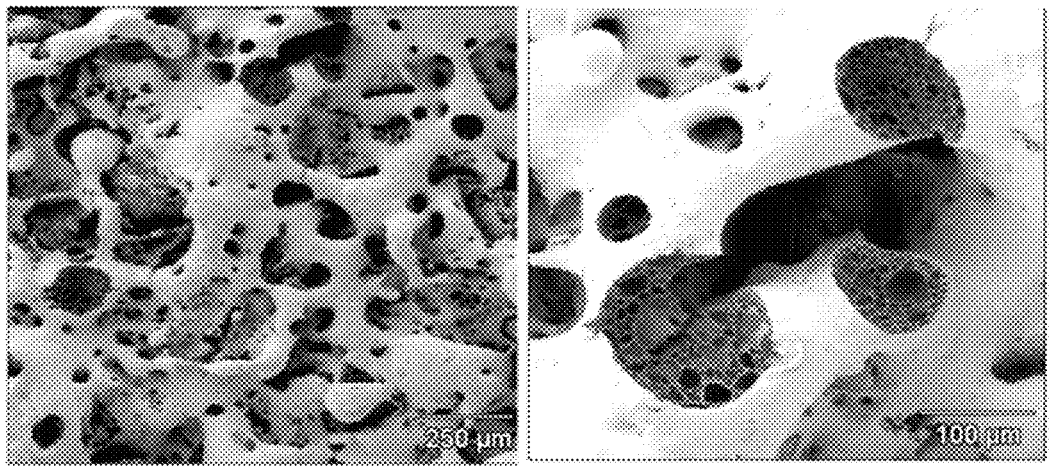
FIG. 10. SEM photographs of patches prepared by melt processing and freeze/phase inversion.
Figure 10:
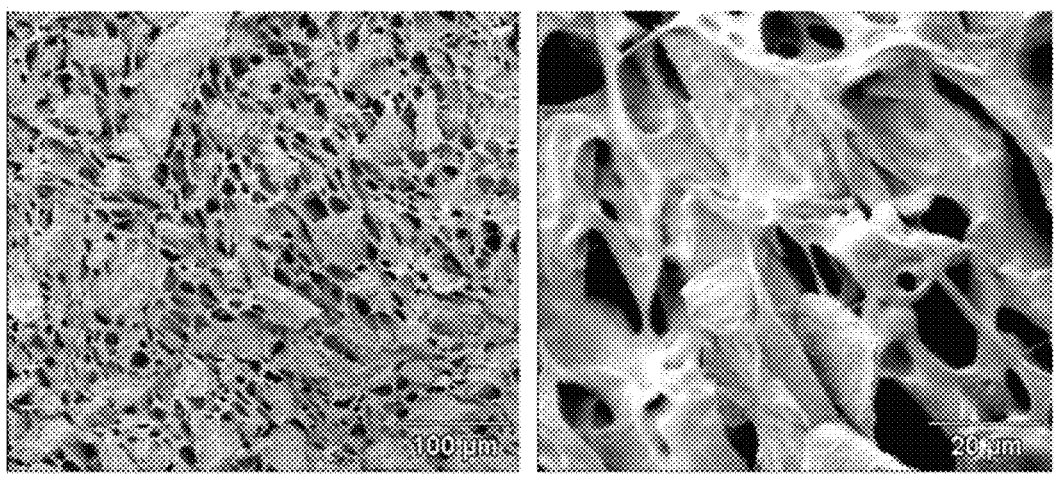
Figure 11:
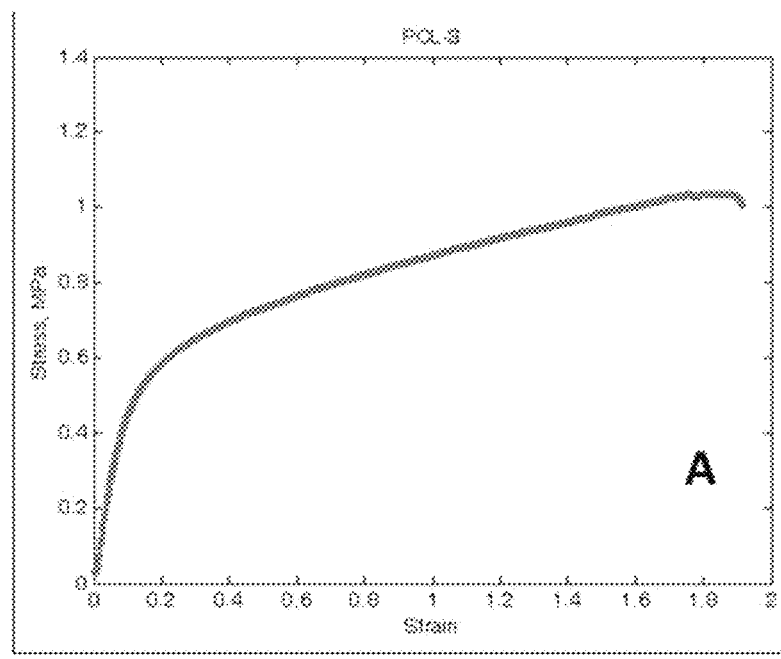
FIG. 11. Stress-strain curves: A) PCL-3 (PCL+chitosan+plasticizer+bioglass) and B) copolymer 3 (L-lactide/ε-caprolactone chitosan+plasticizer+bioglass).
Figure 11:
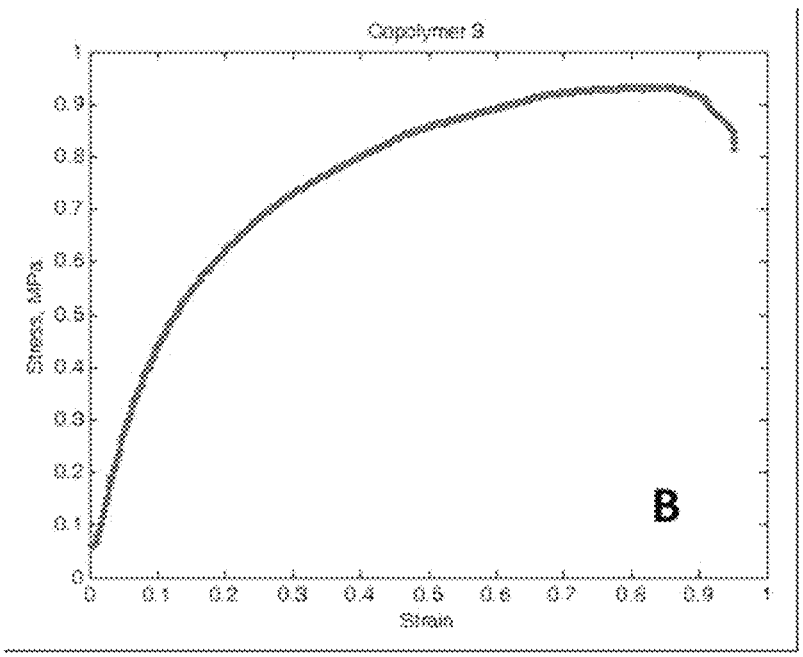
Figure 11:
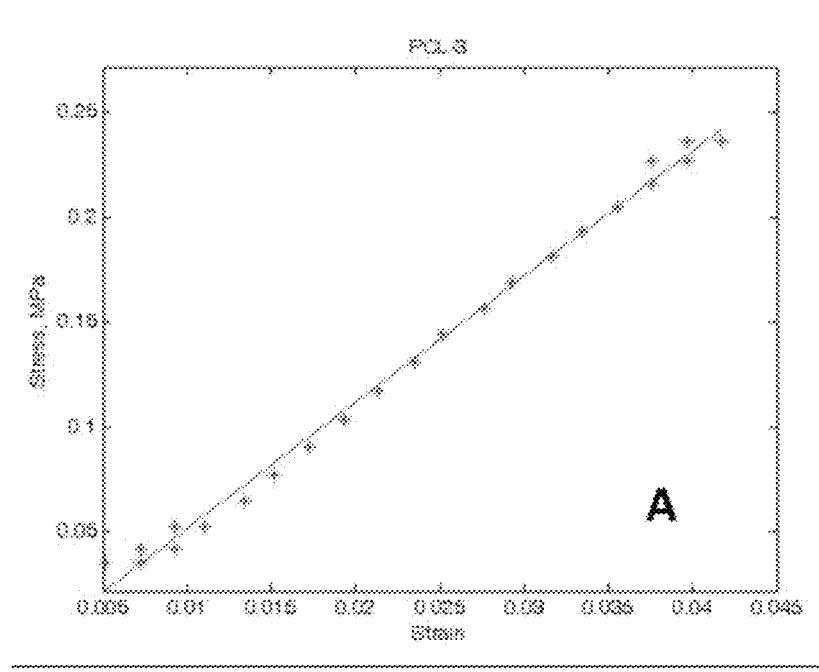
Figure 11:
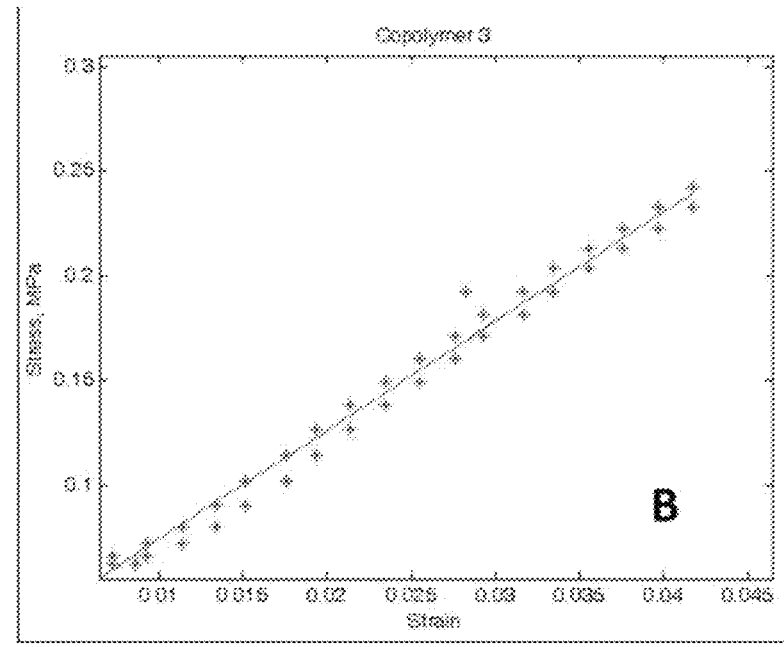
Figure 12:
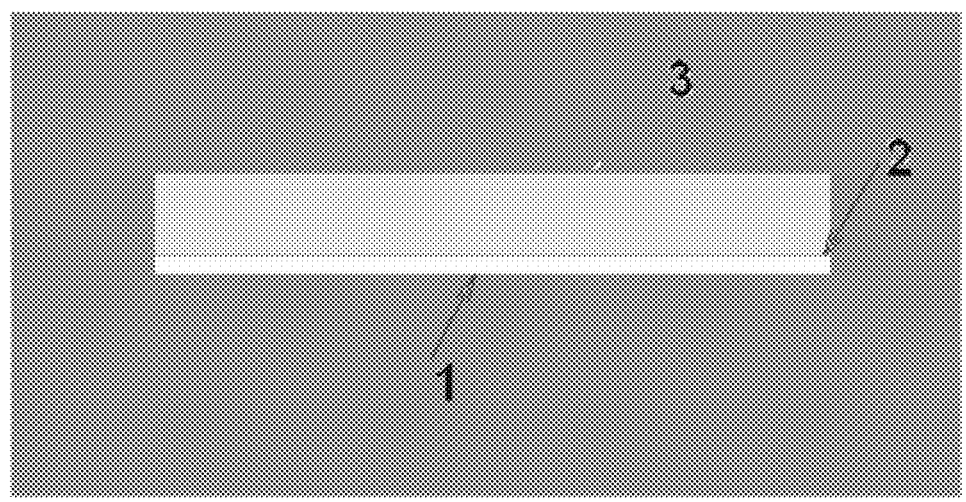
FIG. 12: Supported cardiac patch concept: 1) a biodegradable film of PEUUs; 2) primer adhesive of poly(hydroxyurethane); 3) PCL based composites structures with impregnated self assemble peptide gels.
Figure 13:
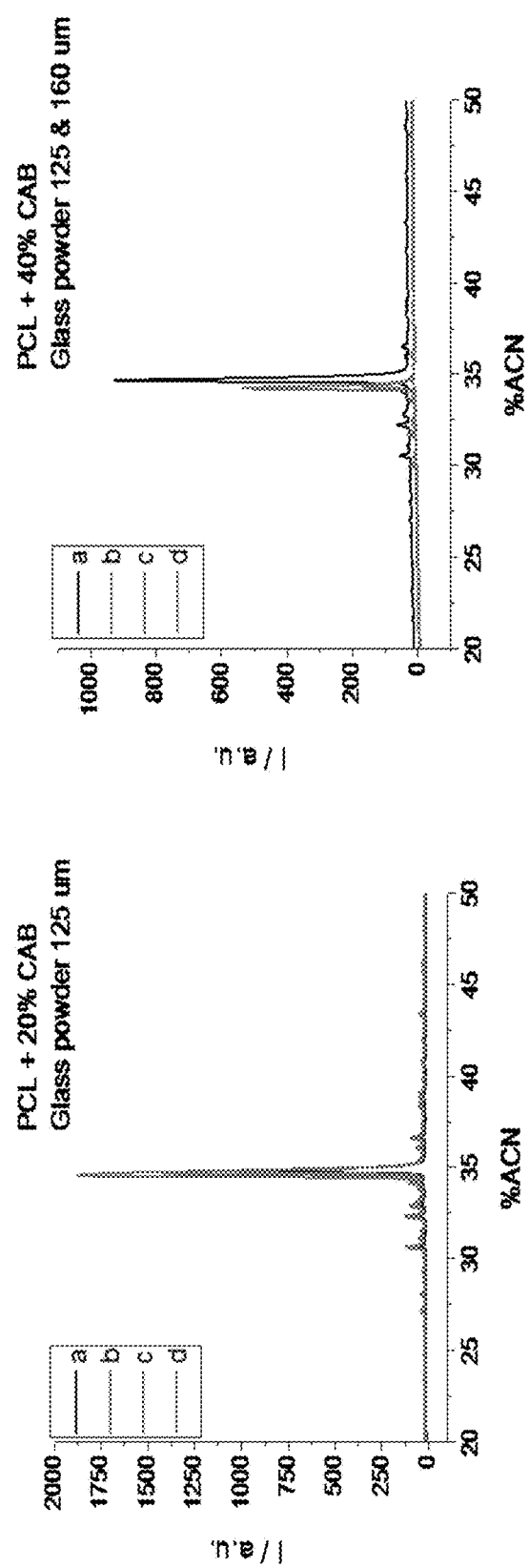
FIG. 13: Evaluation of SEQ ID NO: 1 (FEFEFKFK) content in PCL/CAB systems
Figure 14:
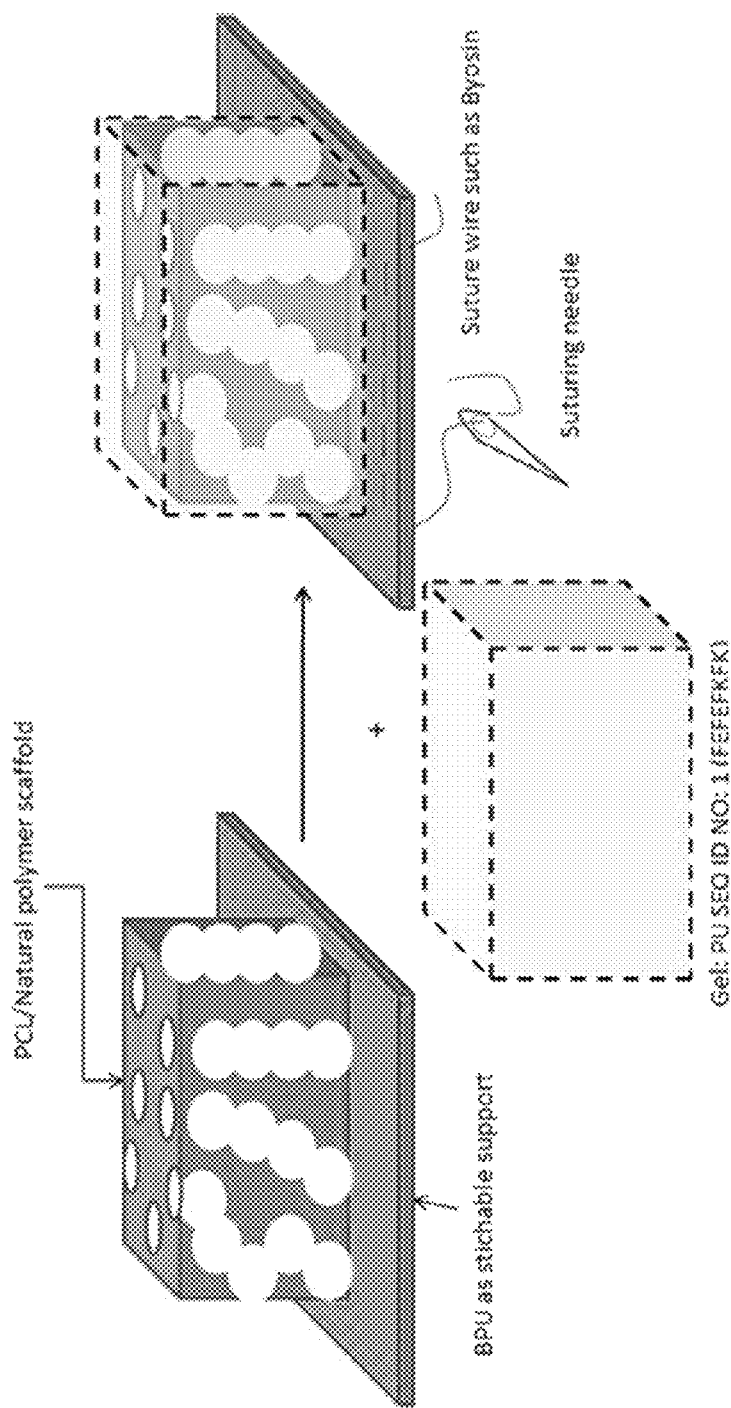
FIG. 14: schematic representation of a 3 components cardiac patch
Figure 15:
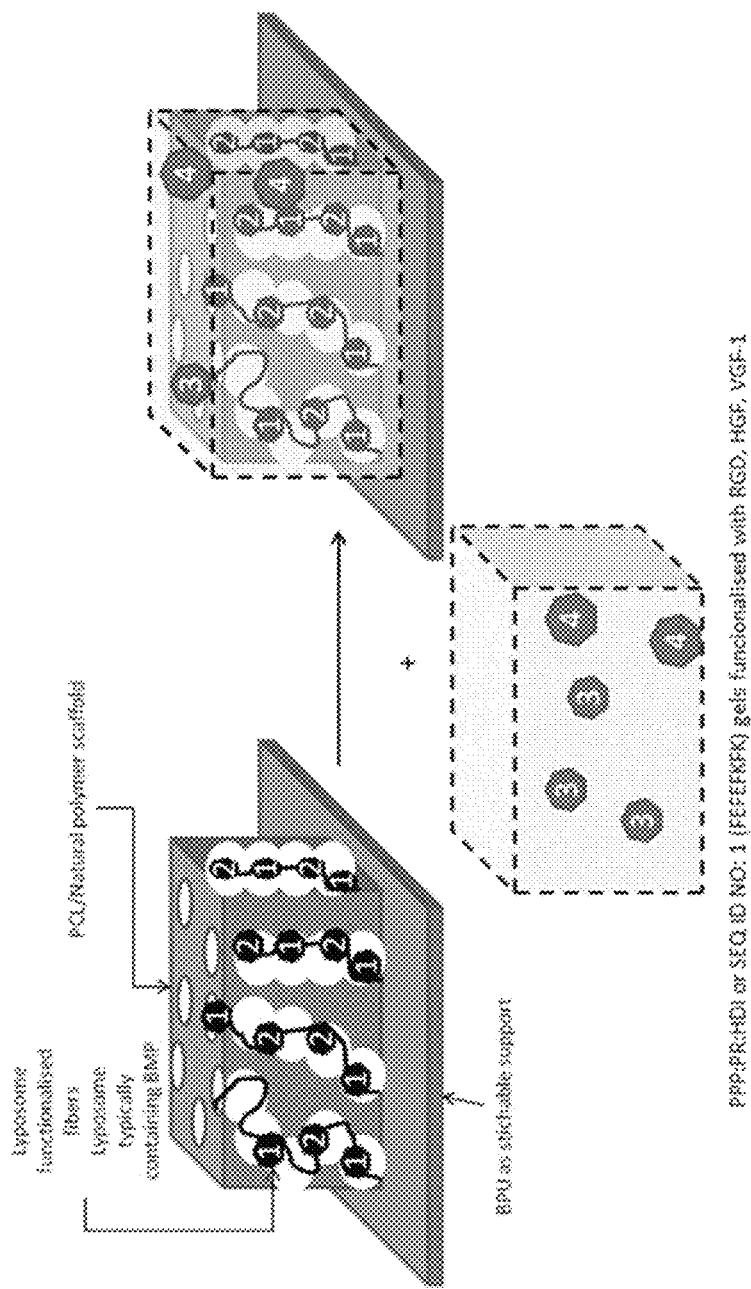
FIG. 15: schematic representation of a 4 component cardiac patch, where numbering represent sites of chemical and/or biological cues.
Figure 16:
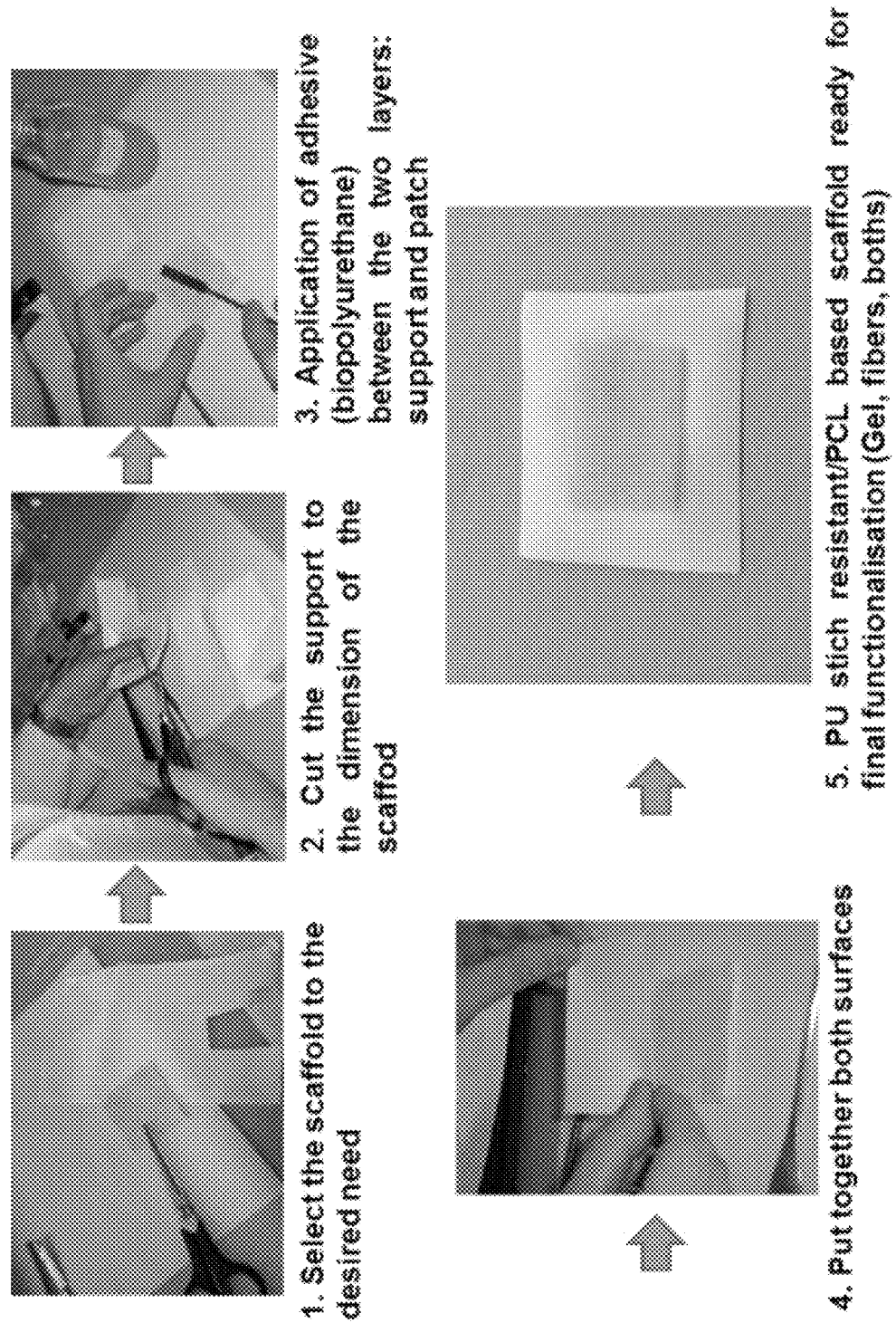
FIG. 16: Step by step representation of the preparation of stichable cardiac patch with 3D scaffold polyurethane support and bio-polyurethane adhesive.
Figure 17:
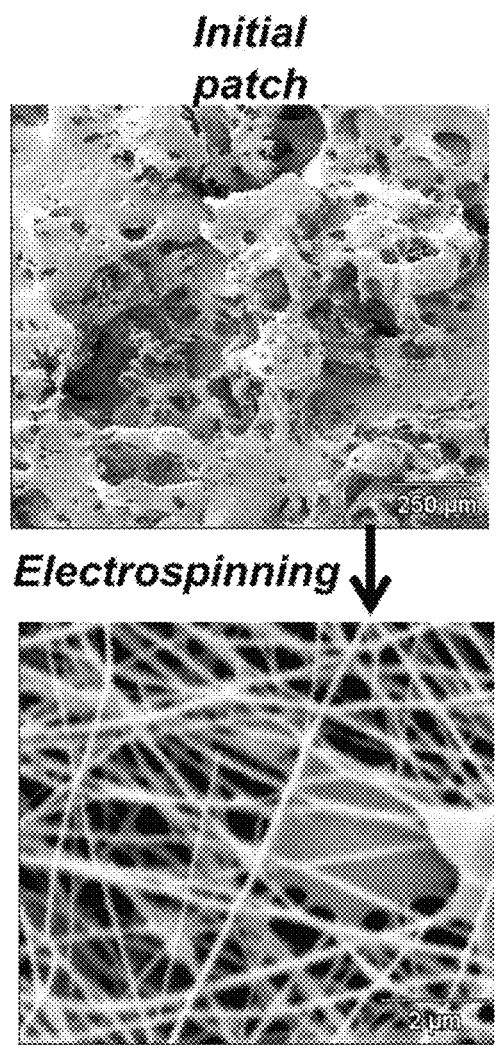
FIG. 17: SEM photographs of patch before and after deposition of electrospun nano fibres and release profile of cardiac patch+coaxial nano fibres PCL/PVA charged with FITC dextran.
Figure 17:
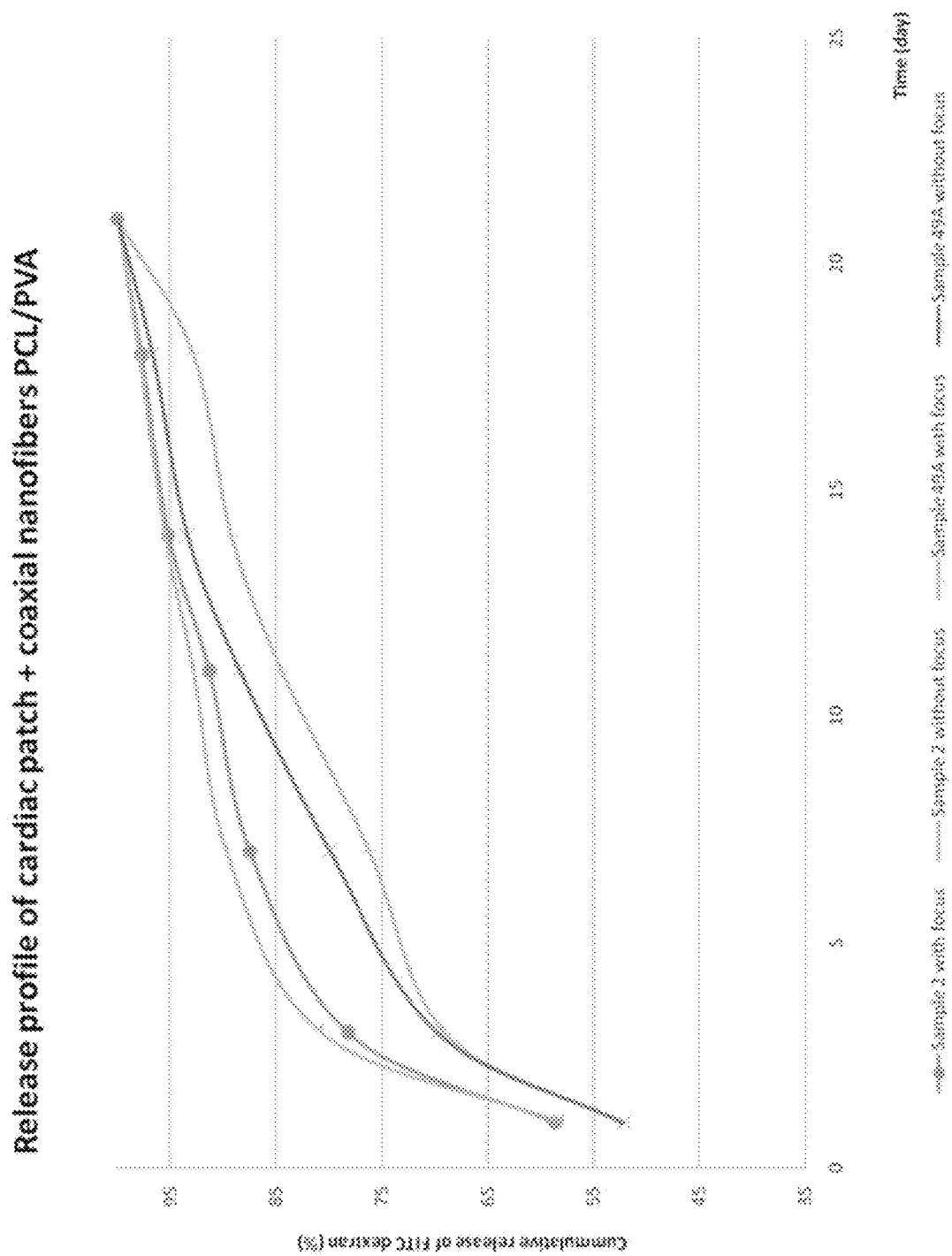
Figure 18:
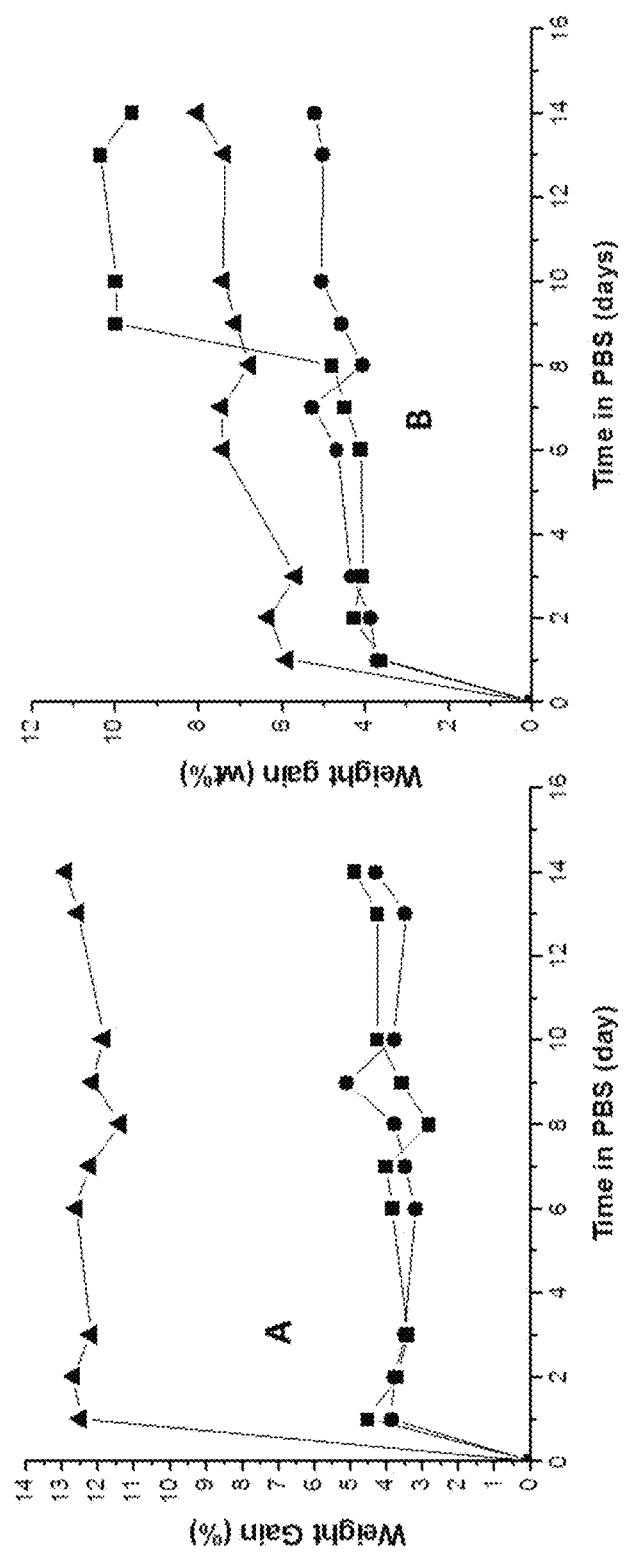
FIG. 18. Percentage weight gain of PCL/cellulose acetyl butyrate blends in PBS medium.
Figure 19:
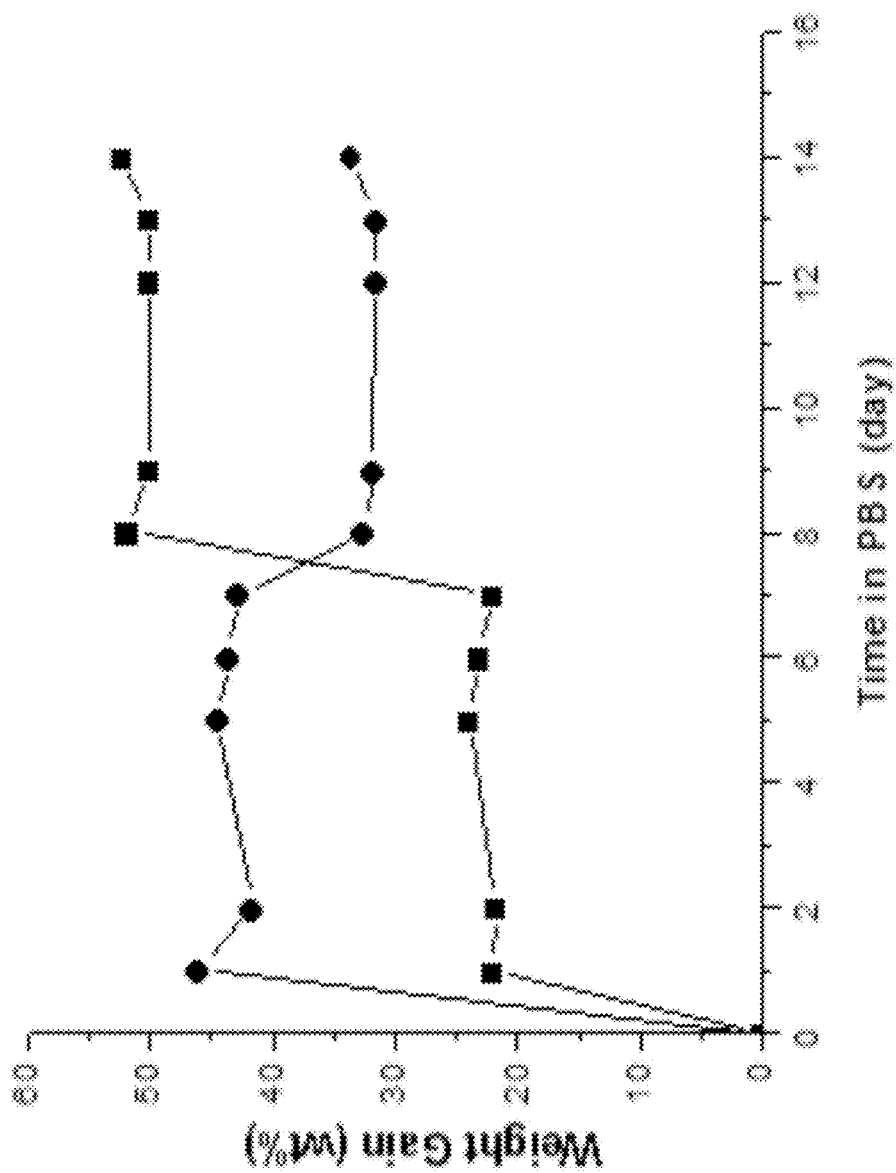

FIG. 19: Percentage weight gain of L-lactide-ε-caprolactone/chitosan blends in PBS medium: (■) 40% chitosan and (●) 20% chitosan. Both blends series were prepared with 20% tributyl citrate, 20% glass powder 125 microns, 20% glass powder 160 microns and 3% NaHCO3 and then treated with HF during 10 minutes.

Figure 20:
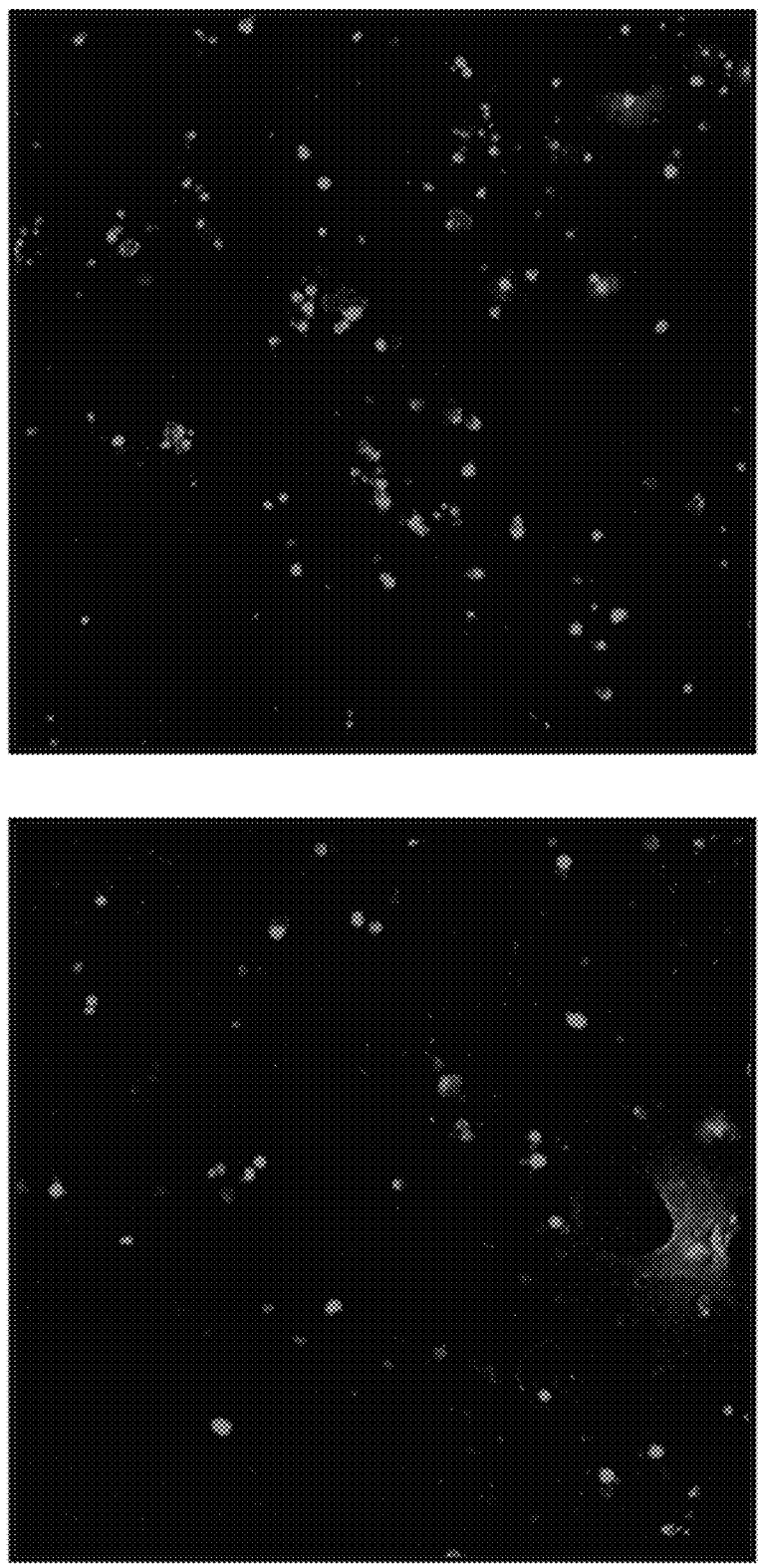
Figure 21:
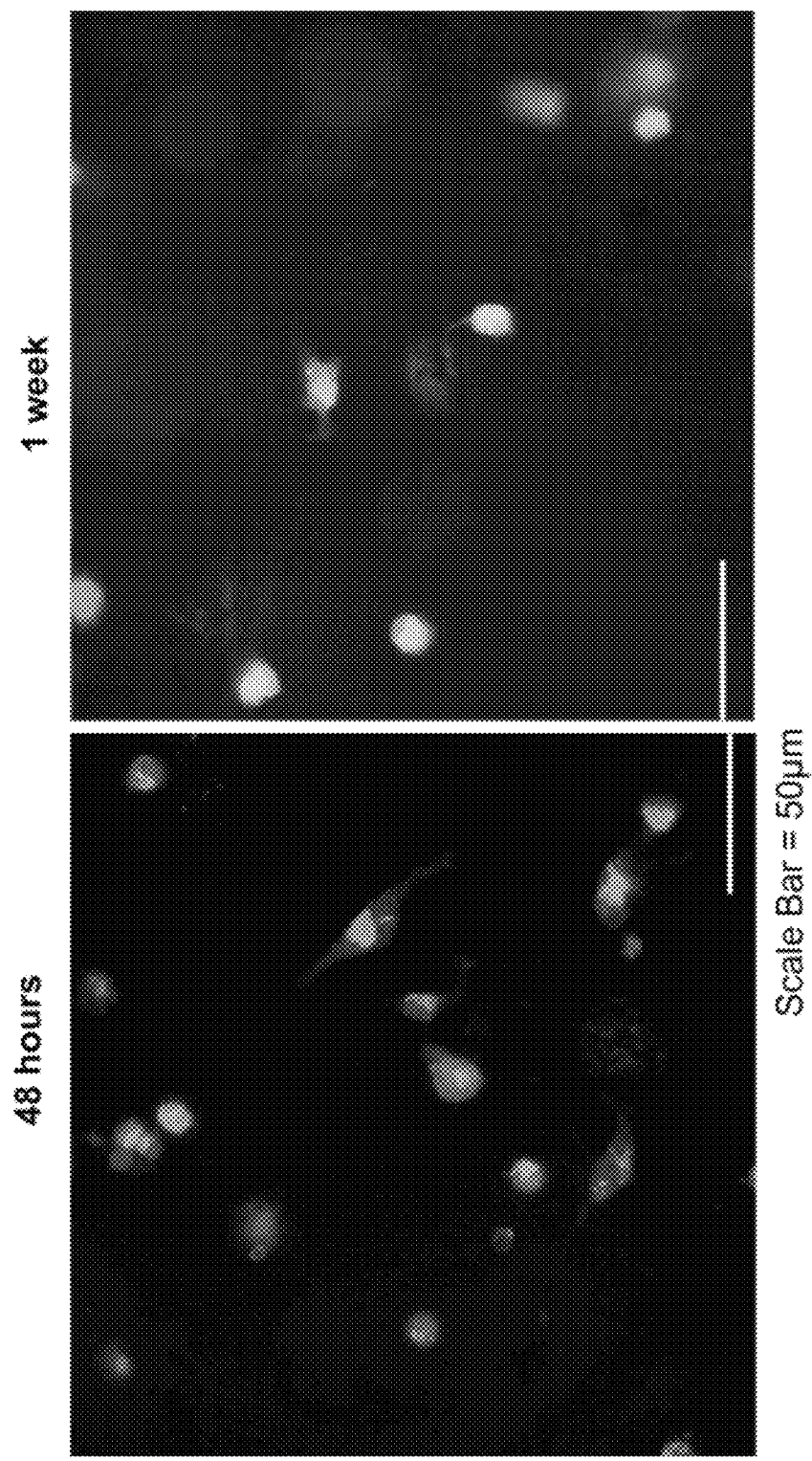

FIG. 20: confocal analysis of 7 days culture of rat Cardiac progenitor Cells (CPC) isolated from the heart and Bone Marrow Progenitor Cells (BMC) form EGFP transgenic rats on (PCL or L-lactide/-caprolactone) alginic acid based cardiac patch. Data kindly supplied by Prof. Quaini, University of Parma FIG. 21: Fluorescent imaging of rAoEC seeded onto poly(ε-caprolactone):chitosan using DIL and eGFP as fluorescent cell tracker.

Figure 22:
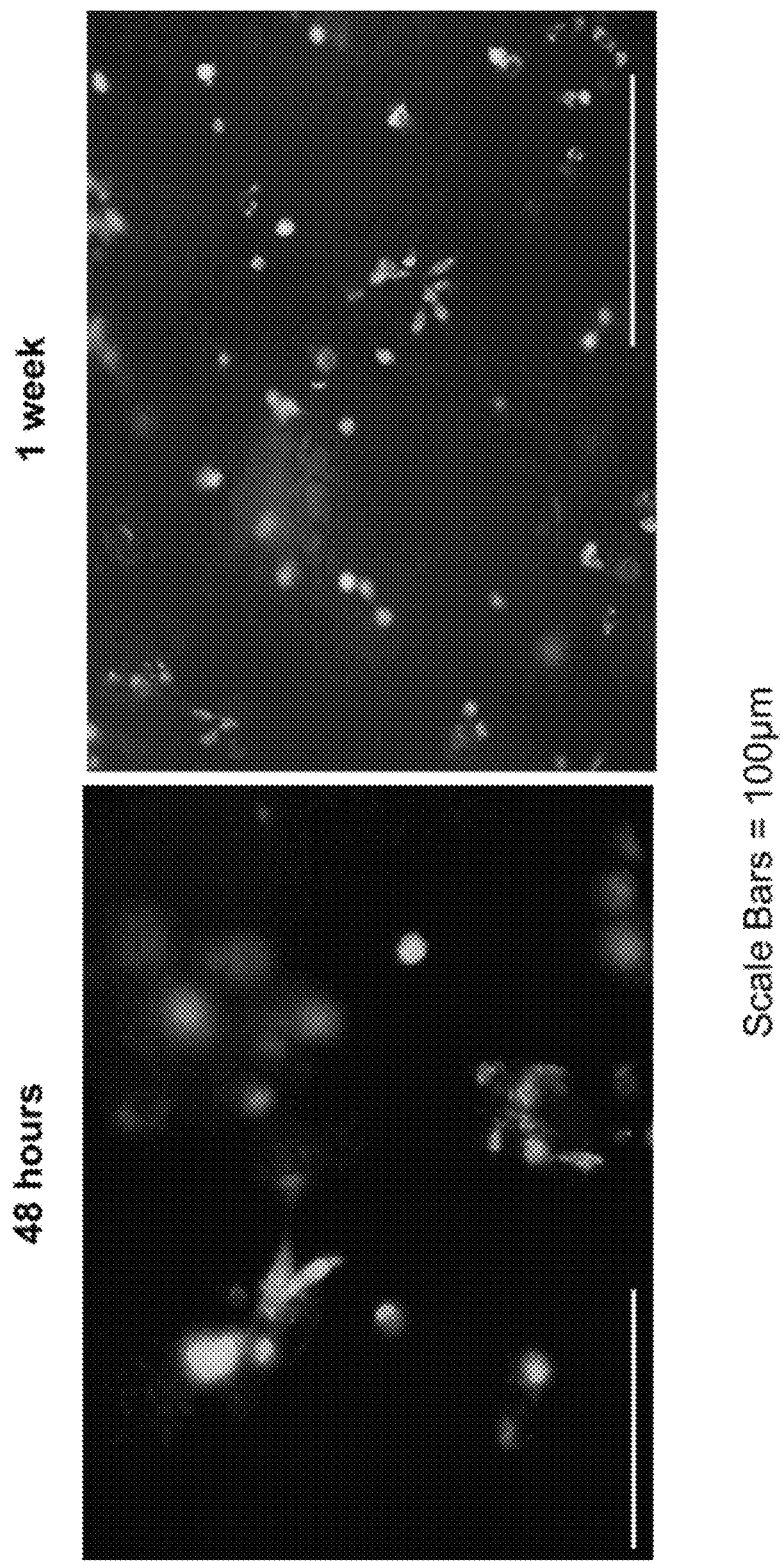
Figure 23:
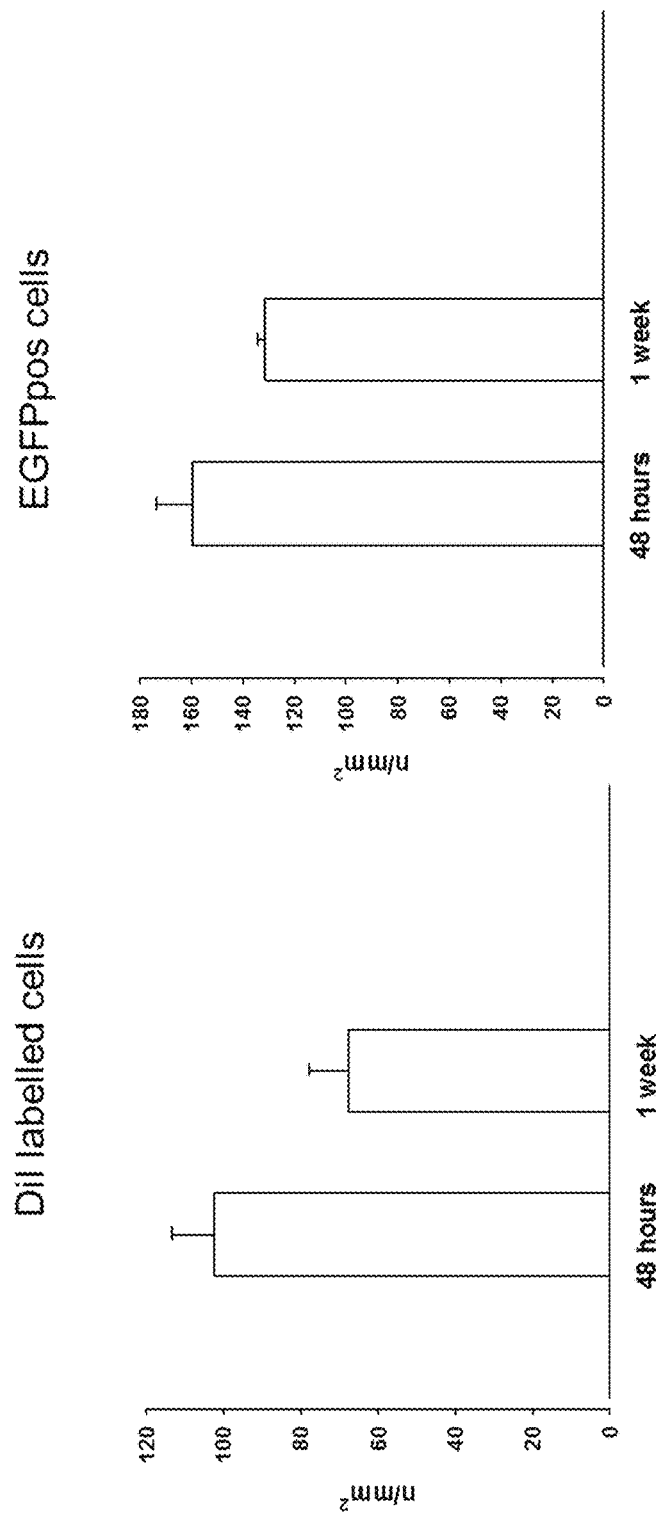
Figure 24:

FIG. 22: Fluorescent imaging of rCPC seeded onto poly (ε-caprolactone):chitosan using DIL and eGFP as fluorescent cell tracker FIG. 23: In Vitro rAoECs/rCPCs survival on proposed scaffold, central element of the cardiac patch FIG. 24: Open chest picture of implanted cardiac patch onto rat animal model at the time of sacrifice.

Figure 25:
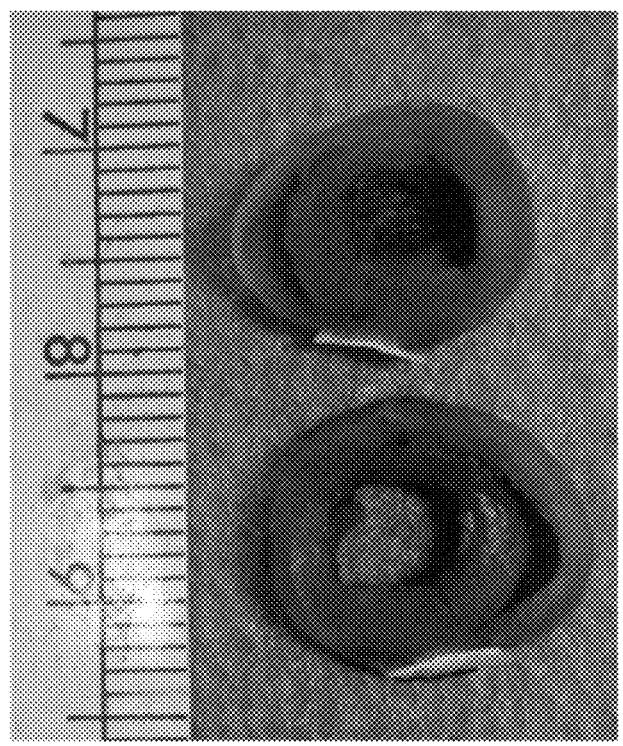
Figure 25:
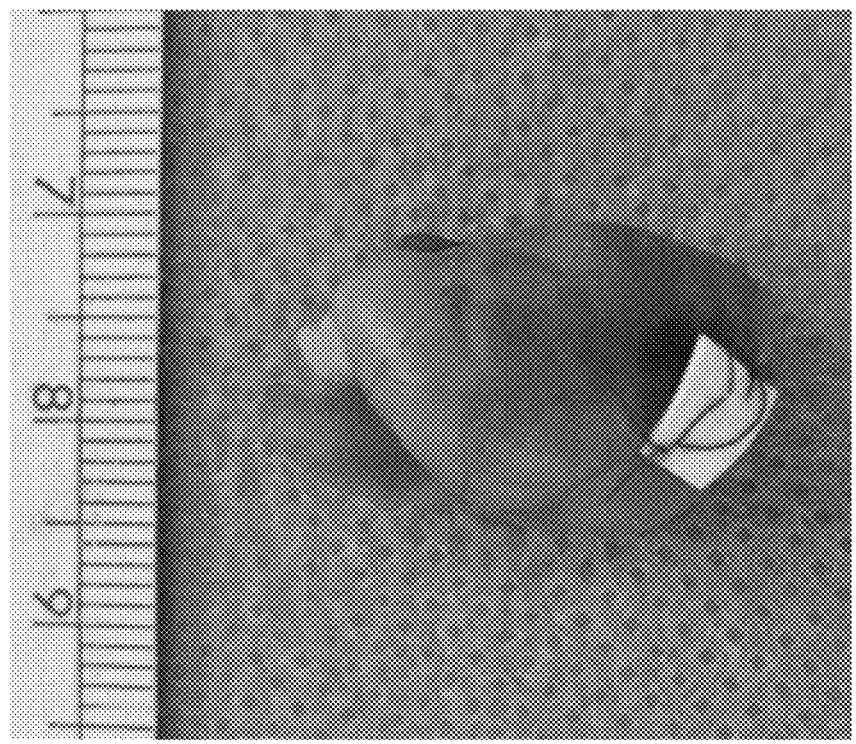
Figure 26:
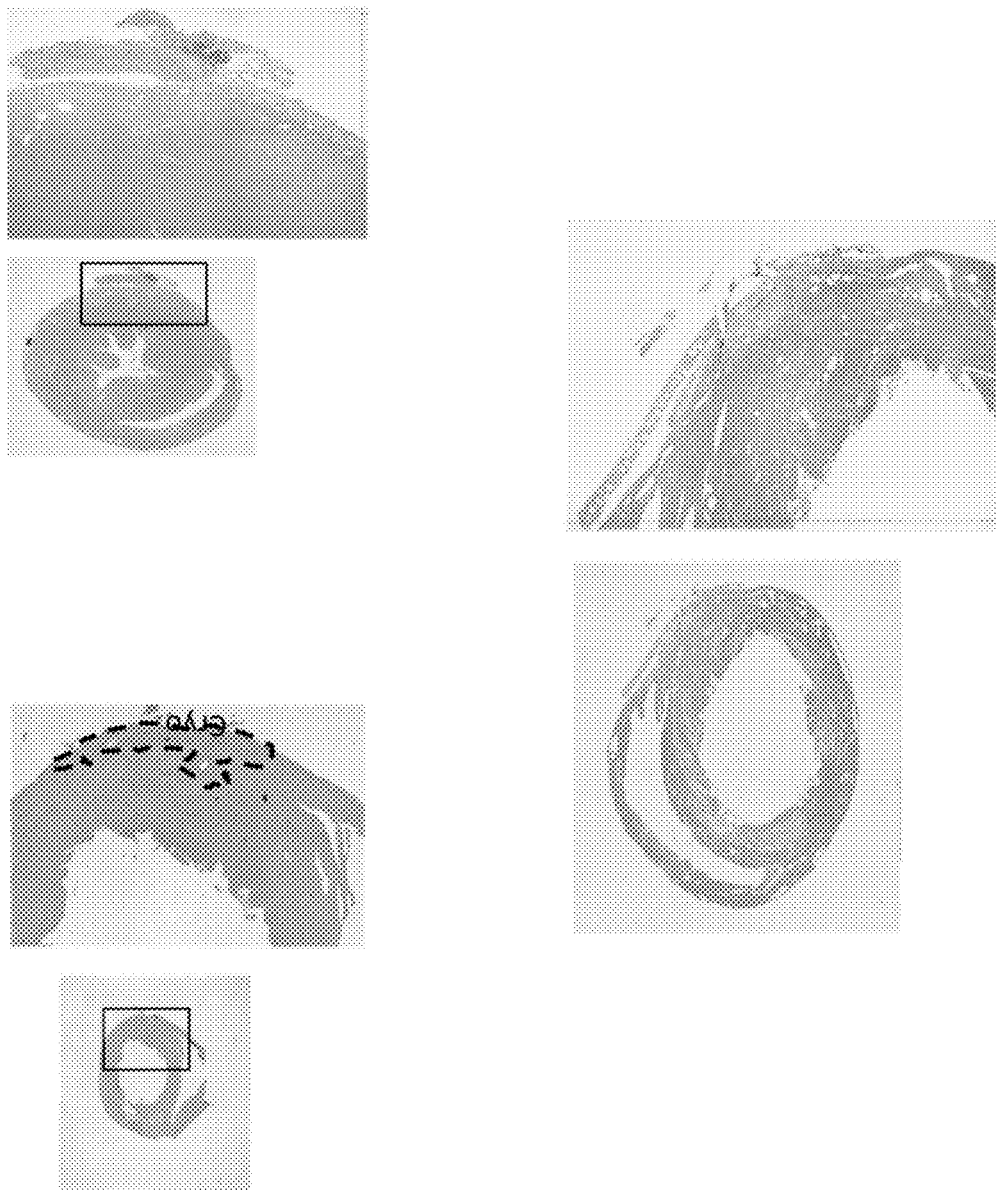

FIG. 25: pictures of rat heart post sacrifice and pre-immunohistochemical characterisation FIG. 26: tissue imaging of injury formation on animal model following cryogenisation of LV, surgical removal of scare tissue and implantation of scaffold (unseeded)

Figure 27:
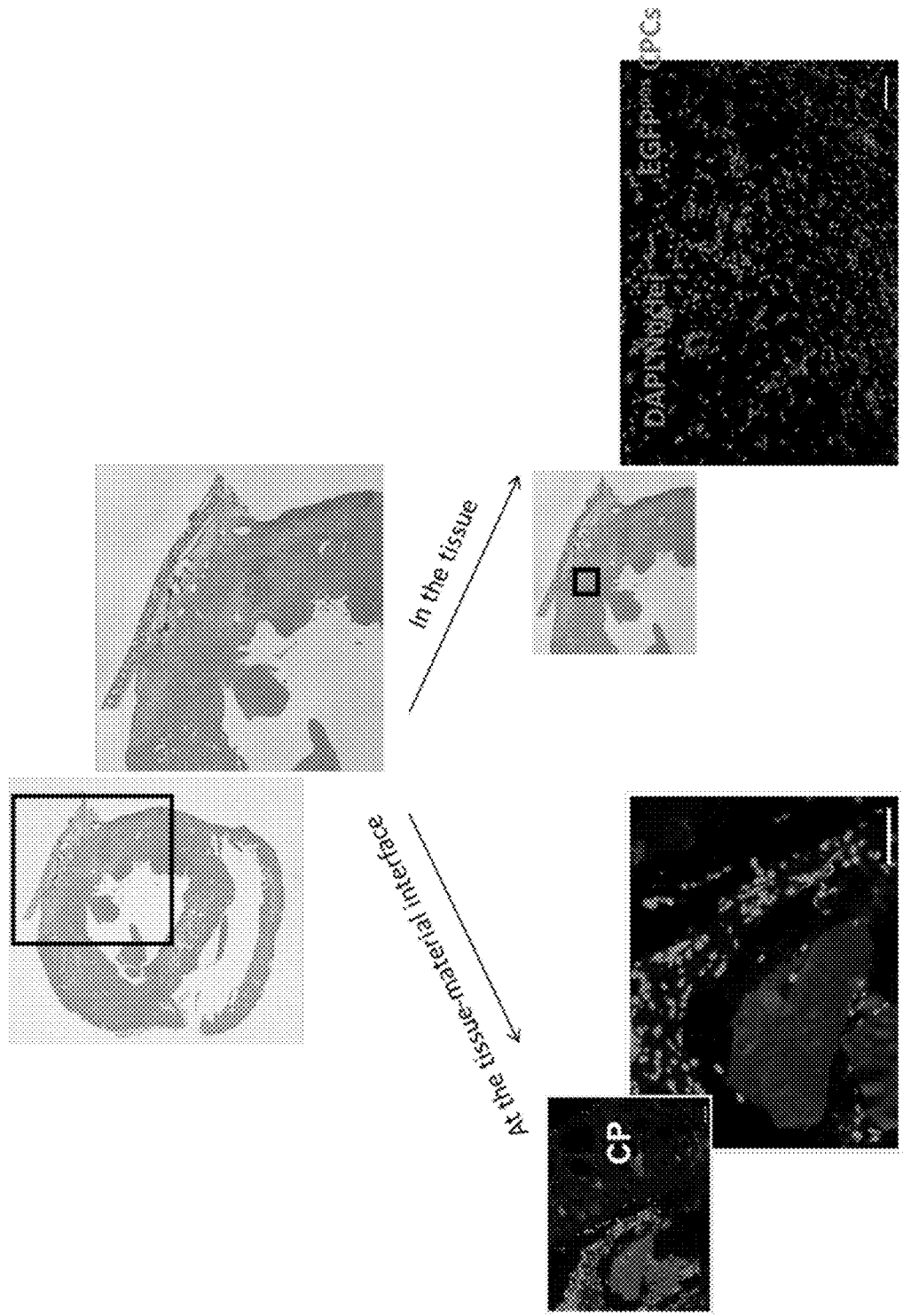

FIG. 27: Immunochemical staining of CPCs that were seed onto a poly(ε-caprolactone):chitosan cardiac patch.

The invention claimed is:

1. A composition comprising:
   a) a biocompatible and biodegradable scaffold comprising synthetic and natural polymers, wherein the synthetic polymer is selected from polylactic acid, poly-glycolic acid, poly-lactone, polyglycerol sebacate, copolymer of synthetic polymers and combinations thereof, and wherein the natural polymer is selected from chitosan, sodium alginate and cellulose;
   b) a hydrogel comprising self assembling peptides, wherein the self assembling peptides are selected from the sequences SEQ ID NO: 1, SEQ ID NO: 2, SEQ ID NO: 3, SEQ ID NO: 4, and combinations thereof; and
   c) a support comprising polyurethane.

2. The composition according to claim 1, wherein the poly-lactone is polycaprolactone (PCL).

3. The composition according to claim 1, wherein the copolymer of synthetic polymers is poly(lactic-co-glycolic acid) (PLGA), and poly(L-lactide)/poly(ε-caprolactone).

4. The composition according to claim 1, wherein the cellulose is cellulose acetyl butyrate (CAB), carboxylated cellulose or cellulose microcrystalline.

5. The composition according to claim 1, wherein the natural polymer is chitosan.

6. The composition according to claim 1, wherein the natural polymer is sodium alginate.

7. The composition according to claim 1, wherein the self assembling peptide is SEQ ID NO: 1.

8. The composition according to claim 1, wherein the support is polyurethane.

9. The composition according to claim 1, which also comprises a plasticizer.

10. The composition according to claim 1, which also comprises glass powder.

11. The composition according to claim 1, which also comprises a foaming agent.

12. The composition according to claim 1, which also comprises fibers wherein said fibers are selected from polyvinylalcohol, polycaprolactone and poly(3,4-ethylenedioxythiopene poly(styrenesulfonate) or combinations thereof.

13. The composition according to claim 1, which also comprises liposomes.

14. The composition according to claim 1, which also comprises at least one trophic agent.

15. The composition according to claim 1, which also comprises at least one growth factor, wherein said growth factor is hepatocyte and/or insulin growth factor.

16. The composition according to claim 1, which also comprises at least one drug, wherein said drug is selected from 5-azacytidine and dexamethasone.

17. The composition according to claim 1, which also comprises cells.

18. The composition according to claim 1 for use in therapy.

19. The composition according to claim 1 for use in the treatment of myocardial infraction, curettage or transmural infarct treatment.

20. A cardiac patch comprising the composition according to claim 1.

* * * * *